US008221347B2

(12) United States Patent
Toles et al.

(10) Patent No.: US 8,221,347 B2
(45) Date of Patent: Jul. 17, 2012

(54) NEEDLE-FREE INJECTOR

(75) Inventors: Warren L. Toles, Clearwater Bay (CA);
Kevin Toles, Winnipeg (CA); Jules Poiron, Somerset, CA (US)

(73) Assignee: AcuShot, Inc., Winnipeg (CA)

( * ) Notice: Subject to any disclaimer, the term of this patent is extended or adjusted under 35 U.S.C. 154(b) by 814 days.

(21) Appl. No.: 11/792,141

(22) PCT Filed: Dec. 1, 2005

(86) PCT No.: PCT/CA2005/001824
§ 371 (c)(1),
(2), (4) Date: Jun. 26, 2008

(87) PCT Pub. No.: WO2006/058426
PCT Pub. Date: Jun. 8, 2006

(65) Prior Publication Data
US 2009/0234276 A1    Sep. 17, 2009

Related U.S. Application Data

(60) Provisional application No. 60/632,316, filed on Dec. 1, 2004.

(51) Int. Cl.
*A61M 5/30* (2006.01)
(52) U.S. Cl. ........................................................ 604/70
(58) Field of Classification Search ............... 604/70
See application file for complete search history.

(56) References Cited

U.S. PATENT DOCUMENTS

| | | | |
|---|---|---|---|
| 2,322,244 A | 6/1943 | Lockhart | |
| 2,322,245 A | 6/1943 | Lockhart | |
| 2,380,534 A | 7/1945 | Lockhart | |
| 2,547,099 A | 4/1951 | Smoot | |
| 2,645,223 A | 7/1953 | Lawshe et al. | |
| 2,667,874 A * | 2/1954 | Dickinson, Jr. | 604/72 |
| 2,704,542 A | 3/1955 | Scherer | |

(Continued)

FOREIGN PATENT DOCUMENTS

CA          492587         5/1953
(Continued)

OTHER PUBLICATIONS

Mexican Office Action, dated Dec. 6, 2010, for Mexican Patent Application No. MX/a/2007/006435 (original language document and English-language translation).

(Continued)

*Primary Examiner* — Theodore Stigell
*Assistant Examiner* — Jason Flick
(74) *Attorney, Agent, or Firm* — Morgan, Lewis & Bockius LLP

(57) ABSTRACT

The present invention provides a needle-free injection device for delivering a medicament under pressure into an animal or human. The injection device includes an actuating device comprising: a gas tight chamber; a piston and rod assembly slidably received in the chamber and movable between a forward position and a rearward position; a gas charge in the chamber for urging the piston and rod assembly to the forward position; means for moving said piston and rod assembly against said gas charge into the rearward position; and a trigger for releasably retaining the piston and assembly in the rearward position. Also provided is a method and kit for using the device to administer a liquid through the skin of an animal or human.

21 Claims, 25 Drawing Sheets

U.S. PATENT DOCUMENTS

| | | |
|---|---|---|
| 3,115,133 A | 12/1963 | Morando |
| 3,308,818 A | 3/1967 | Rutkowski |
| 3,335,722 A | 8/1967 | Lowry et al. |
| 3,527,212 A | 9/1970 | Clark |
| 3,853,125 A | 12/1974 | Clark et al. |
| 3,859,996 A | 1/1975 | Mizzy et al. |
| 3,908,651 A | 9/1975 | Fudge |
| 3,948,266 A | 4/1976 | Clark et al. |
| 4,010,747 A | 3/1977 | Clark et al. |
| 4,044,758 A | 8/1977 | Patel |
| 4,342,310 A | 8/1982 | Lindmayer et al. |
| 4,518,385 A | 5/1985 | Lindmayer et al. |
| 4,560,377 A | 12/1985 | Geat et al. |
| 4,596,556 A | 6/1986 | Morrow et al. |
| 4,623,332 A | 11/1986 | Lindmayer et al. |
| 4,636,198 A | 1/1987 | Stade |
| 4,680,027 A | 7/1987 | Parsons et al. |
| 4,705,509 A | 11/1987 | Stade |
| 4,722,728 A | 2/1988 | Dixon |
| 4,850,967 A | 7/1989 | Cosmai |
| 4,874,367 A | 10/1989 | Edwards |
| 4,913,699 A | 4/1990 | Parsons |
| 5,009,637 A | 4/1991 | Newman et al. |
| 5,024,656 A | 6/1991 | Gasaway et al. |
| 5,026,343 A | 6/1991 | Holzer |
| 5,064,413 A | 11/1991 | McKinnon et al. |
| 5,073,165 A | 12/1991 | Edwards |
| 5,269,762 A | 12/1993 | Armbruster et al. |
| 5,312,335 A | 5/1994 | McKinnon et al. |
| 5,322,511 A | 6/1994 | Armbruster et al. |
| 5,334,144 A | 8/1994 | Alchas et al. |
| 5,360,413 A | 11/1994 | Leason et al. |
| 5,383,851 A | 1/1995 | McKinnon, Jr. et al. |
| 5,399,163 A | 3/1995 | Peterson et al. |
| 5,480,381 A | 1/1996 | Weston |
| 5,499,972 A | 3/1996 | Parsons |
| 5,501,666 A | 3/1996 | Spielberg |
| 5,503,628 A | 4/1996 | Fetters et al. |
| 5,520,639 A | 5/1996 | Peterson et al. |
| 5,542,920 A | 8/1996 | Cherif Cheikh |
| 5,569,189 A | 10/1996 | Parsons |
| 5,599,302 A | 2/1997 | Lilley et al. |
| 5,601,077 A | 2/1997 | Imbert |
| 5,630,796 A | 5/1997 | Bellhouse et al. |
| 5,704,911 A | 1/1998 | Parsons |
| 5,730,723 A | 3/1998 | Castellano et al. |
| 5,779,668 A | 7/1998 | Grabenkort |
| 5,846,233 A | 12/1998 | Lilley et al. |
| 5,851,198 A | 12/1998 | Castellano et al. |
| 5,879,327 A | 3/1999 | DeFarges et al. |
| 5,891,085 A | 4/1999 | Lilley et al. |
| 5,891,086 A | 4/1999 | Weston |
| 5,899,880 A | 5/1999 | Bellhouse et al. |
| 5,919,159 A | 7/1999 | Lilley et al. |
| 5,957,886 A | 9/1999 | Weston |
| 5,993,412 A | 11/1999 | Deily et al. |
| 6,004,286 A | 12/1999 | Bellhouse et al. |
| 6,004,287 A * | 12/1999 | Loomis et al. ................ 604/68 |
| 6,013,050 A | 1/2000 | Bellhouse et al. |
| 6,042,571 A | 3/2000 | Hjertman et al. |
| 6,053,890 A | 4/2000 | Defarges et al. |
| 6,063,053 A | 5/2000 | Castellano et al. |
| 6,080,130 A | 6/2000 | Castellano |
| 6,096,002 A | 8/2000 | Landau |
| 6,117,443 A | 9/2000 | Cherif-Cheikh |
| 6,120,786 A | 9/2000 | Cherif Cheikh |
| 6,123,685 A | 9/2000 | Reynolds |
| 6,132,395 A | 10/2000 | Landau et al. |
| 6,135,979 A | 10/2000 | Weston |
| 6,168,587 B1 | 1/2001 | Bellhouse et al. |
| 6,171,276 B1 | 1/2001 | Lippe et al. |
| 6,210,359 B1 | 4/2001 | Patel et al. |
| 6,223,408 B1 | 5/2001 | Vetter et al. |
| 6,223,786 B1 | 5/2001 | Castellano |
| 6,251,091 B1 | 6/2001 | Weston |
| 6,258,063 B1 | 7/2001 | Haar et al. |
| 6,264,629 B1 | 7/2001 | Landau |
| 6,270,473 B1 | 8/2001 | Schwebel |
| 6,309,371 B1 | 10/2001 | Deboer et al. |
| 6,383,168 B1 | 5/2002 | Landau et al. |
| 6,406,455 B1 | 6/2002 | Willis et al. |
| 6,440,099 B2 | 8/2002 | Haar et al. |
| 6,440,101 B1 | 8/2002 | Grabenkort et al. |
| 6,447,475 B1 | 9/2002 | Castellano |
| 6,454,746 B1 | 9/2002 | Bydlon et al. |
| 6,471,669 B2 | 10/2002 | Landau |
| 6,474,369 B2 | 11/2002 | Castellano |
| 6,475,181 B1 | 11/2002 | Potter et al. |
| 6,506,177 B2 | 1/2003 | Landau |
| 6,537,245 B1 | 3/2003 | Alexandre et al. |
| 6,544,545 B1 | 4/2003 | Cherif-Cheikh |
| 6,547,755 B1 | 4/2003 | Lippe et al. |
| 6,558,348 B2 | 5/2003 | Parsons |
| 6,572,581 B1 | 6/2003 | Landau |
| 6,585,685 B2 | 7/2003 | Staylor et al. |
| 6,599,264 B1 | 7/2003 | Erni et al. |
| 6,602,222 B1 | 8/2003 | Roser |
| 6,613,010 B2 | 9/2003 | Castellano |
| 6,613,011 B2 | 9/2003 | Castellano |
| 6,616,627 B2 | 9/2003 | Willis et al. |
| 6,620,135 B1 * | 9/2003 | Weston et al. ................ 604/140 |
| 6,641,554 B2 | 11/2003 | Landau |
| 6,645,170 B2 | 11/2003 | Landau |
| 6,648,850 B2 | 11/2003 | Landau |
| 6,673,034 B2 | 1/2004 | Castellano |
| 6,673,035 B1 | 1/2004 | Rice et al. |
| 6,673,038 B2 | 1/2004 | Weston |
| 6,676,630 B2 | 1/2004 | Landau et al. |
| 6,682,504 B2 | 1/2004 | Nelson et al. |
| 6,689,093 B2 | 2/2004 | Landau |
| 6,689,095 B1 | 2/2004 | Garitano et al. |
| 6,689,101 B2 | 2/2004 | Hjertman et al. |
| 6,706,031 B2 | 3/2004 | Manera |
| 6,729,370 B2 | 5/2004 | Norton et al. |
| 6,740,062 B2 | 5/2004 | Hjertman |
| 6,752,781 B2 | 6/2004 | Landau et al. |
| 6,758,829 B2 | 7/2004 | Alexandre et al. |
| 6,770,054 B1 | 8/2004 | Smolyarov et al. |
| 6,783,509 B1 | 8/2004 | Landau et al. |
| 6,824,526 B2 | 11/2004 | Castellano |
| 6,835,187 B2 | 12/2004 | Alexandre et al. |
| 6,881,200 B2 | 4/2005 | Bellhouse et al. |
| 7,150,409 B2 * | 12/2006 | Gonnelli et al. ................ 239/1 |
| 2001/0002433 A1 | 5/2001 | Weston |
| 2001/0004681 A1 | 6/2001 | Landau |
| 2001/0004682 A1 | 6/2001 | Weston |
| 2001/0018935 A1 | 9/2001 | Castellano |
| 2001/0027290 A1 | 10/2001 | Weston |
| 2001/0031945 A1 | 10/2001 | Haar et al. |
| 2001/0039394 A1 | 11/2001 | Weston |
| 2001/0051789 A1 | 12/2001 | Parsons |
| 2002/0004639 A1 | 1/2002 | Willis et al. |
| 2002/0007142 A1 | 1/2002 | Hjertman et al. |
| 2002/0035348 A1 | 3/2002 | Hjertman |
| 2002/0055712 A1 | 5/2002 | Neracher |
| 2002/0056486 A1 | 5/2002 | Castellano |
| 2002/0058907 A1 | 5/2002 | Deboer et al. |
| 2002/0091353 A1 | 7/2002 | Bellhouse et al. |
| 2002/0095121 A1 | 7/2002 | Norton et al. |
| 2002/0099329 A1 | 7/2002 | Castellano |
| 2002/0123717 A1 | 9/2002 | Landau |
| 2002/0123718 A1 | 9/2002 | Landau |
| 2002/0151839 A1 | 10/2002 | Landau |
| 2002/0151840 A1 | 10/2002 | Castellano |
| 2002/0151841 A1 | 10/2002 | Castellano |
| 2002/0151842 A1 | 10/2002 | Gonnelli et al. |
| 2002/0156418 A1 | 10/2002 | Gonnelli et al. |
| 2002/0161329 A1 | 10/2002 | Gonnelli et al. |
| 2002/0161334 A1 | 10/2002 | Castellano et al. |
| 2002/0169412 A1 | 11/2002 | Haar et al. |
| 2002/0183689 A1 | 12/2002 | Alexandre et al. |
| 2002/0188248 A1 | 12/2002 | Bellhouse et al. |
| 2002/0188249 A1 | 12/2002 | Landau |
| 2002/0188250 A1 | 12/2002 | Landau et al. |
| 2002/0188251 A1 | 12/2002 | Staylor et al. |
| 2002/0189612 A1 | 12/2002 | Rand |
| 2003/0000524 A1 | 1/2003 | Anderson et al. |

| Publication No. | Date | Inventor |
|---|---|---|
| 2003/0005926 A1 | 1/2003 | Jones et al. |
| 2003/0014006 A1 | 1/2003 | Alexandre et al. |
| 2003/0040697 A1 | 2/2003 | Pass et al. |
| 2003/0040715 A1 | 2/2003 | D'Antonio et al. |
| 2003/0050596 A1 | 3/2003 | Alexandre et al. |
| 2003/0054044 A1 | 3/2003 | Potter et al. |
| 2003/0055395 A1 | 3/2003 | Manera |
| 2003/0065286 A1 | 4/2003 | Landau |
| 2003/0078535 A1 | 4/2003 | Castellano |
| 2003/0078536 A1 | 4/2003 | Alexandre et al. |
| 2003/0079744 A1 | 5/2003 | Bonney et al. |
| 2003/0082216 A1 | 5/2003 | Cherif-Cheikh |
| 2003/0083612 A1 | 5/2003 | Castellano |
| 2003/0088207 A1 | 5/2003 | Rogatchev et al. |
| 2003/0088214 A1 | 5/2003 | Leon et al. |
| 2003/0093030 A1 | 5/2003 | Landau |
| 2003/0097093 A1 | 5/2003 | Navelier et al. |
| 2003/0114789 A1 | 6/2003 | Haar et al. |
| 2003/0135155 A1 | 7/2003 | Alexandre et al. |
| 2003/0149396 A1 | 8/2003 | Alexandre et al. |
| 2003/0149397 A9 | 8/2003 | Gonnelli et al. |
| 2003/0163111 A1 | 8/2003 | Daellenbach |
| 2003/0187386 A1 | 10/2003 | Parsons |
| 2003/0225368 A1 | 12/2003 | Landau et al. |
| 2004/0015125 A1 | 1/2004 | Alexandre et al. |
| 2004/0015126 A1 | 1/2004 | Zierenberg et al. |
| 2004/0024350 A1 | 2/2004 | Brouillette |
| 2004/0025871 A1 | 2/2004 | Davies |
| 2004/0039367 A1 | 2/2004 | Alexandre et al. |
| 2004/0049151 A1 | 3/2004 | Lell |
| 2004/0087897 A1 | 5/2004 | Hjertman |
| 2004/0111054 A1 | 6/2004 | Landau et al. |
| 2004/0111055 A1 | 6/2004 | Daellenbach |
| 2004/0112457 A1 | 6/2004 | Norton et al. |
| 2004/0133150 A1 | 7/2004 | Hjertman et al. |
| 2004/0134563 A1 | 7/2004 | Rice et al. |
| 2004/0134564 A1 | 7/2004 | Mitchell et al. |
| 2004/0158195 A1 | 8/2004 | Sibert et al. |
| 2004/0158196 A1 | 8/2004 | Garitano et al. |
| 2004/0162517 A1 | 8/2004 | Furst et al. |
| 2004/0176721 A1 | 9/2004 | Furst et al. |
| 2004/0186432 A1 | 9/2004 | Barry et al. |
| 2004/0193105 A1 | 9/2004 | Geiger |
| 2004/0199106 A1 | 10/2004 | Landau et al. |
| 2004/0215135 A1 | 10/2004 | Sheldrake et al. |
| 2004/0215136 A1 | 10/2004 | Navelier et al. |
| 2004/0215137 A1 | 10/2004 | Navelier et al. |
| 2004/0215149 A1 | 10/2004 | Hjertman |
| 2004/0220525 A1 | 11/2004 | Willis et al. |
| 2004/0249339 A1 | 12/2004 | Willis et al. |
| 2004/0254526 A1 | 12/2004 | Weston |
| 2005/0010167 A1 | 1/2005 | Alexandre et al. |
| 2005/0010168 A1 | 1/2005 | Kendall |
| 2005/0013840 A1 | 1/2005 | Potter et al. |
| 2005/0020984 A1 | 1/2005 | Lesch |
| 2005/0038394 A1 | 2/2005 | Schwarzbich |
| 2005/0075601 A1 | 4/2005 | Landau et al. |
| 2005/0083611 A1 | 4/2005 | Shum et al. |

FOREIGN PATENT DOCUMENTS

| | | |
|---|---|---|
| CA | 494217 | 7/1953 |
| CA | 516456 | 9/1955 |
| CA | 516714 | 9/1955 |
| CA | 519101 | 12/1955 |
| CA | 523736 | 4/1956 |
| CA | 535723 | 1/1957 |
| CA | 569887 | 2/1959 |
| CA | 570045 | 2/1959 |
| CA | 591271 | 1/1960 |
| CA | 591272 | 1/1960 |
| CA | 600186 | 6/1960 |
| CA | 607962 | 11/1960 |
| CA | 610087 | 12/1960 |
| CA | 629262 | 10/1961 |
| CA | 667536 | 7/1963 |
| CA | 690652 | 7/1964 |
| CA | 726463 | 1/1966 |
| CA | 739231 | 7/1966 |
| CA | 972649 | 8/1975 |
| CA | 1040040 | 10/1978 |
| CA | 1045490 | 1/1979 |
| CA | 1061213 | 8/1979 |
| CA | 1157332 | 11/1983 |
| CA | 1178503 | 11/1984 |
| CA | 1196244 | 11/1985 |
| CA | 1228519 | 10/1987 |
| CA | 1232807 | 2/1988 |
| CA | 1258019 | 8/1989 |
| CA | 1261219 | 9/1989 |
| CA | 1265401 | 2/1990 |
| CA | 2028870 | 5/1991 |
| CA | 1284752 | 6/1991 |
| CA | 1300453 | 5/1992 |
| CA | 1310870 | 5/1992 |
| CA | 2095858 | 5/1992 |
| CA | 2097919 | 6/1992 |
| CA | 2091945 | 10/1993 |
| CA | 1326983 | 2/1994 |
| CA | 1333553 | 12/1994 |
| CA | 2176490 | 5/1995 |
| CA | 2199516 | 3/1996 |
| CA | 2199417 | 5/1996 |
| CA | 2215278 | 9/1996 |
| CA | 2074219 | 10/1996 |
| CA | 2108326 | 3/1997 |
| CA | 2234482 | 4/1997 |
| CA | 2240581 | 6/1997 |
| CA | 2251256 | 10/1997 |
| CA | 2278136 | 7/1998 |
| CA | 2123829 | 2/1999 |
| CA | 2162909 | 5/1999 |
| CA | 2261078 | 8/1999 |
| CA | 2261079 | 8/1999 |
| CA | 2321906 | 9/1999 |
| CA | 2116341 | 12/1999 |
| CA | 2340883 | 3/2000 |
| CA | 2343515 | 3/2000 |
| CA | 2351084 | 5/2000 |
| CA | 2257320 | 6/2000 |
| CA | 2353948 | 6/2000 |
| CA | 2296925 | 8/2000 |
| CA | 2368142 | 8/2000 |
| CA | 2367337 | 9/2000 |
| CA | 2370276 | 10/2000 |
| CA | 2159452 | 11/2000 |
| CA | 2387326 | 4/2001 |
| CA | 2387893 | 5/2001 |
| CA | 2392598 | 5/2001 |
| CA | 2396569 | 7/2001 |
| CA | 2331030 | 8/2001 |
| CA | 2405164 | 10/2001 |
| CA | 2407056 | 10/2001 |
| CA | 2408132 | 11/2001 |
| CA | 2409091 | 11/2001 |
| CA | 2410468 | 12/2001 |
| CA | 2411814 | 12/2001 |
| CA | 2021567 | 2/2002 |
| CA | 2324045 | 4/2002 |
| CA | 2423647 | 4/2002 |
| CA | 2425150 | 4/2002 |
| CA | 2427145 | 5/2002 |
| CA | 2430499 | 7/2002 |
| CA | 2433992 | 7/2002 |
| CA | 2372319 | 9/2002 |
| CA | 2021566 | 10/2002 |
| CA | 2444275 | 10/2002 |
| CA | 2455164 | 2/2003 |
| CA | 2456484 | 2/2003 |
| CA | 2459459 | 3/2003 |
| CA | 2464459 | 5/2003 |
| CA | 2464954 | 5/2003 |
| CA | 2468283 | 6/2003 |
| CA | 2469640 | 6/2003 |
| CA | 2371466 | 8/2003 |
| CA | 2476076 | 8/2003 |
| CA | 2477373 | 9/2003 |
| CA | 2479316 | 9/2003 |
| CA | 2479409 | 9/2003 |

| | | |
|---|---|---|
| CA | 2380671 | 10/2003 |
| CA | 2481434 | 10/2003 |
| CA | 2430449 | 11/2003 |
| CA | 2486398 | 12/2003 |
| CA | 2167586 | 1/2005 |
| CA | 2234055 | 2/2005 |
| CA | 2477512 | 2/2005 |
| CA | 2214807 | 5/2005 |
| CA | 2259560 | 7/2005 |
| CA | 2197711 | 11/2005 |
| CA | 2259442 | 6/2006 |
| CA | 2140772 | 7/2006 |
| CA | 2290777 | 7/2006 |
| CA | 2457756 | 7/2006 |
| CA | 2239515 | 9/2006 |
| CA | 2426700 | 2/2007 |
| CA | 2216926 | 4/2007 |
| CA | 2292719 | 4/2007 |
| CA | 2314674 | 5/2007 |
| CA | 2400071 | 6/2007 |
| CA | 2398552 | 7/2007 |
| CA | 2247142 | 9/2007 |
| CA | 2395272 | 9/2007 |
| CA | 2406560 | 9/2007 |
| CA | 2295755 | 10/2007 |
| CA | 2298739 | 10/2007 |
| CA | 2395349 | 11/2007 |
| CA | 2404360 | 12/2007 |
| CA | 2187198 | 1/2008 |
| EP | 0347190 | 12/1989 |
| GB | 731572 | 6/1995 |
| JP | HEI10-512165 | 11/1998 |
| JP | 2000-93513 | 4/2000 |
| JP | 2003-528024 | 9/2003 |
| NZ | 509936 A | 8/2002 |
| WO | WO 94/13345 | 6/1994 |
| WO | WO 96/21482 | 7/1996 |
| WO | WO 99/13345 | 3/1999 |
| WO | WO 99/31262 | 6/1999 |

OTHER PUBLICATIONS

Japanese Office Action, dated Jan. 25, 2011, for Japanese Patent Application No. 2007-543670 (original language document and English-language translation).

Japanese Office Action, dated Jun. 10, 2011, for Japanese Patent Application No. JP 2007-543670 (original language document and English-language translation).

Supplementary European Search Report for EP 05815186, dated Mar. 2, 2011.

Examination Communication issued in a related European Application No. 05815186.1, dated Feb. 8, 2012.

* cited by examiner

Pressure pattern of inventive device

NEEDLE-FREE INJECTOR

The present application is a U.S. National Phase Application of International Application No. PCT/CA2005/001824 (filed Dec. 1, 2005) which claims the benefit of U.S. Provisional Application No. 60/632,316 (filed Dec. 1, 2004), both of which are hereby incorporated by reference in their entirety.

FIELD OF THE INVENTION

The present invention pertains to the field of needle-free injectors.

BACKGROUND

Injections of medicaments are typically carried out using needle-containing injectors. There are a variety of problems associated with needle-containing injectors including cross-contamination of subjects receiving an injection, the pain associated with such injections and the potential for the needles to break, and dislodge, within a subject being injected. The breakage of a needle within a subject can be not only detrimental to the health and wellbeing of the subject, but can also have significant economic impact.

Increasingly, efforts have been directed to developing needle-free injectors, in attempt to avoid problems associated with needle-containing injectors in current use. Typically, such needle-free injectors are powered by an external gas supply so to provide sufficient energy to drive the liquid through the skin. The requirement of an external gas supply can be disadvantageous for the user, as it can be cumbersome and not amenable for use within an enclosure such as an office, laboratory, barn or the like. It can also be inconvenient to store of these types of external power supplies. Additionally, previous needle-free injectors are typically complicated in design, which in turn results in increased cost of manufacture.

There remains a need, therefore, for improved needle-free injectors.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a needle-free injection device. In accordance with one aspect of the present invention there is provided a needle-free injection device for delivering a medicament under pressure from a dosing reservoir through an outlet orifice for administration to an animal and/or human, of the type comprising a plunger slidably received in said dosing reservoir and movable in a forward direction for expelling said medicament through said orifice, the improvement comprising an actuating device disposed on said needle-free injection device, said actuating device comprising: a gas tight chamber; piston and rod assembly slidably received in the chamber and movable between a forward position and a rearward position; a gas charge in the chamber for urging the piston and rod assembly to the forward position; means for moving the piston and rod assembly against the gas charge into the rearward position; and a trigger for releasably retaining the piston and rod assembly in the rearward position, whereby activating the trigger causes the piston and rod assembly to be released for movement by the gas charge to the forward position so as to impact the plunger, directly or indirectly, with a force sufficient to cause the plunger to move in the forward direction to expel the medicament through said outlet.

In accordance with one embodiment of the present invention the circumference of the piston of said piston and rod assembly defines an outer edge that is in contact with the interior surface of said gas tight chamber such that the piston defines an extension portion and a compression portion of said gas tight chamber.

In accordance with another embodiment of the present invention the needle-free device comprises a gap-coupling connecting the rod of the piston and rod assembly to the plunger, wherein said gap-coupling is configured to maintain a gap-distance between said rod and said plunger when said piston and rod assembly is in said rearward position. Preferably the gap-coupling comprises a first end for removable attachment of the gap-coupling to said rod; and a second end for sliding engagement with the plunger.

In accordance with a specific embodiment of the present invention the device includes a manual means for moving the piston and rod assembly against the gas charge, which comprises: (a) a handle pivotally connected to said needle-free injection device and pivotable from a first closed position to a second open position; (b) a push rod pivotally attached to said handle; and (c) an actuating member operatively associated with the rod of said piston and rod assembly and configured to move in response to engagement with the push rod, whereby when said handle is moved from said first closed position to said second position said push rod engages said actuating member and when said handle is returned to said closed position a pushing force is transferred to said push rod, which in turn transfers the pushing force to said actuating member to move said piston and rod assembly from said forward position to said rearward position.

In accordance with an alternate embodiment of the present invention, the manual means comprises a handle pivotally connected to said needle-free injection device and pivotable from a first closed position to a second open position; an actuating member operatively associated with the rod of said piston and rod assembly; and a force transfer means for transferring force applied to the handle to a gear assembly operatively associated with said handle, whereby when said handle is moved from said first closed position to said second open position said gear assembly transfers force generated by movement of the handle to said actuating member to move said piston and rod assembly from said forward position to said rearward position.

Alternatively, the means for moving said piston and rod assembly is a motorized means, for example a DC or AC power supply.

In accordance with another embodiment of the present invention, the needle-free injection device further comprises a gear assembly driven by a motor; and an actuating member operatively associated with the rod of said piston and rod assembly, whereby said motor transfers a force to said gear assembly, which transfers the force to said actuating member to move said piston and rod assembly from said forward position to said rearward position.

In accordance with another specific embodiment of the present invention the trigger comprises a triggering lever having a first end and a second end and being pivotable about a pivot member and connected at said first end to said push rod, whereby when a downward force is exerted on said second end of said triggering lever it pivots about said pivot member and said first end is raised causing said push rod to disengage said actuating member such that said piston and rod assembly moves from said rearward position to said forward position.

In accordance with another aspect of the present invention, there is provided a method of injecting a medicament into an animal/human, comprising: (a) providing an actuated needle-free injection device, as described herein and having a medicament within said dosing chamber; (b) placing the outlet orifice of the injection device against said animal at a site for administration; and (c) triggering said injection device such that said medicament is expelled through said outlet orifice.

In accordance with another aspect of the present invention, there is provided a kit for the use of a needle-free injection device as described herein, comprising: (a) the needle-free injection device; and (b) instructions for the use thereof.

BRIEF DESCRIPTION OF THE FIGURES

FIG. 3A depicts the actuation device before being mounted in the housing of the needle-free injection device. FIG. 3B depicts the actuation device mounted in the housing of the needle-free injection device, wherein the actuation device is in an uncharged condition. FIG. 3C depicts the same actuation device as depicted in FIG. 3B after charging of the device by the user, such that the piston and rod assembly is in the rearward position.

FIG. 4A depicts an exploded view of the plunger, gap-coupling and connector. FIGS. 4B and 4C depicts the plunger slidingly received within the gap-coupling, the gap-coupling is attached to the connector, which is in turn connected to the rod.

FIGS. 5A and 5B depict the handle in the first closed position and second open position, respectively.

Figure 1:
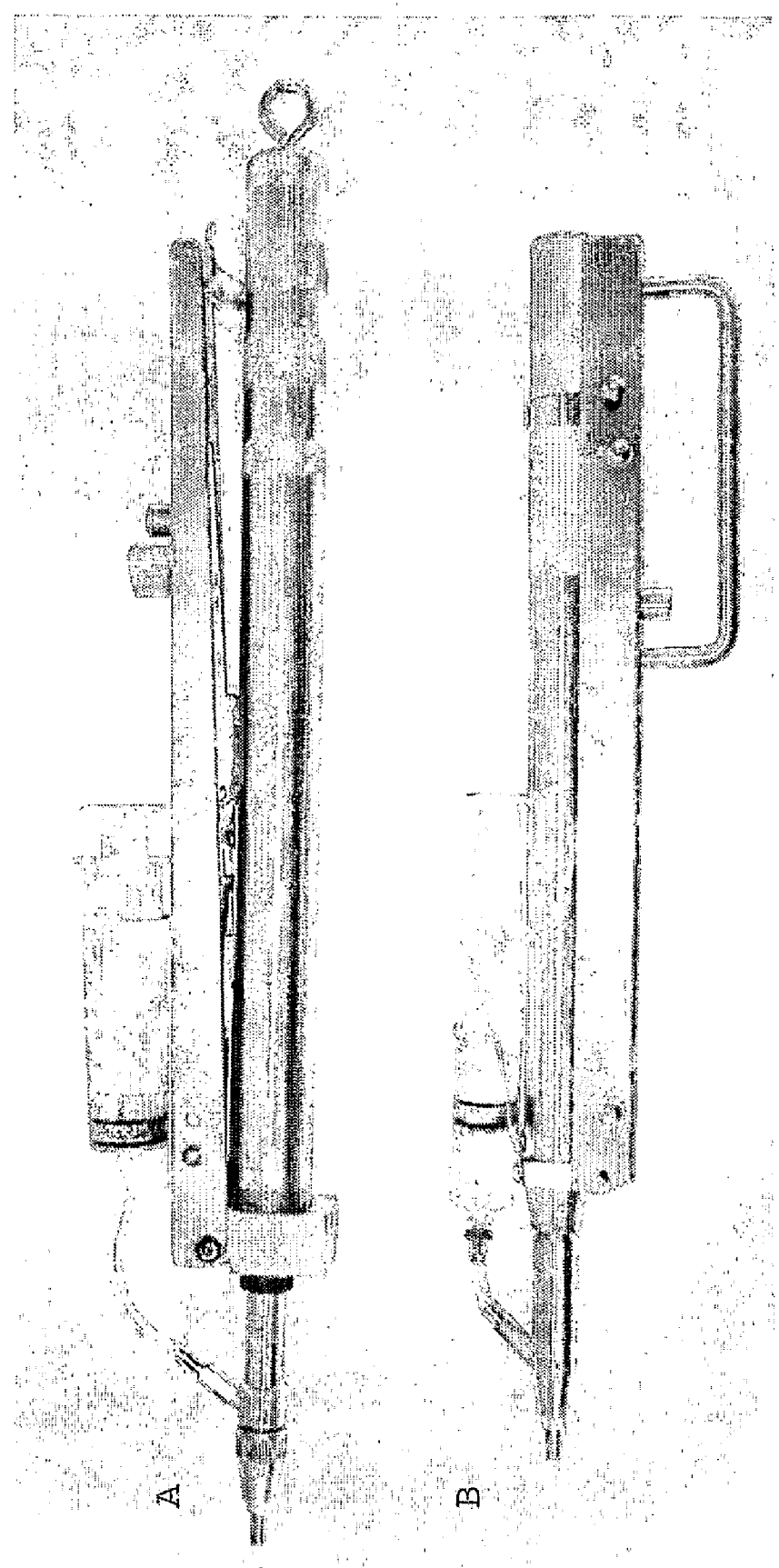
FIG. 1A is a photograph of a needle-free injection device according to one embodiment of the present invention and FIG. 1B is a photograph of a needle-free injection device according to another embodiment of the present invention.

In the Detailed Description that follows the numbers in bold face type serve to identify the component parts that are described and referred to in relation to the drawings depicting various embodiments of the invention. It should be noted that in describing various embodiments of the present invention, the same reference numerals have been used to identify the same or similar elements. Moreover, for the sake of simplicity, parts have been omitted from some figures of the drawings.

DETAILED DESCRIPTION OF THE INVENTION

As will be explained in more detail below, the present invention provides a needle-free injection device for injecting a medicament under pressure into a human or animal. The device of the present invention comprises some of the features of standard needle-free injection devices including a dosing reservoir for the medicament, and an outlet orifice in the dosing reservoir through which the medicament is expelled for administration to the animal or human. As in certain needle-free injection devices known in the art, the device of the present invention makes use of a plunger slidably received in the dosing reservoir and movable forward for expelling the medicament through the outlet orifice. In the device of the present invention, these features are combined with an actuating device comprising a gas tight chamber having a piston and rod assembly slidably received therein, a gas charge in the gas tight chamber for urging the piston and rod assembly to a forward position, means for moving the piston and rod assembly against the gas charge to a rearward position and a trigger for releasably retaining the piston and rod assembly in the rearward position, such that when the trigger is released, the piston and rod assembly moves to the forward position so as to impact the plunger, directly or indirectly, with sufficient force to move the plunger forward to expel medicament from the dosing reservoir and through the skin of the human or animal being treated.

All or a portion of the needle-free injection device is preferably sized to be portable, for example hand-held, thereby allowing a user to move from subject to subject (e.g., a human or an animal) to perform injections. Alternatively, all or a portion of the needle-free device may be permanently or removably attached to a structure, such as an injection station, thereby allowing the user to bring the subjects to the injection station to receive an injection. In certain applications it may also be beneficial to have only the dosing portion of the device sized to be hand-held by a user. In this embodiment, the actuating portion remains operatively associated with the dosing portion.

Referring to the FIGS. 1-10, the needle-free injection device comprises a dosing reservoir 16 for receiving a liquid, such as a medicament. Reservoir 16 has a discharge end having an outlet orifice having nozzle 17, through which the liquid in the reservoir may be expelled for administration to an animal or human. Optionally, nozzle 17 is removably attached to the discharge end of dosing reservoir 16, for example via a screw fit. Optionally, reservoir 16 has an inlet opening through which the liquid may be received. Dosing reservoir 16 can be sized to accommodate a range of volumes of liquid. Additionally, dosing reservoir 16 may be removable so as to facilitate the use of reservoirs of varied sizes and/or material suitable for different volumes or different liquids depending on specific applications.

Figure 2:
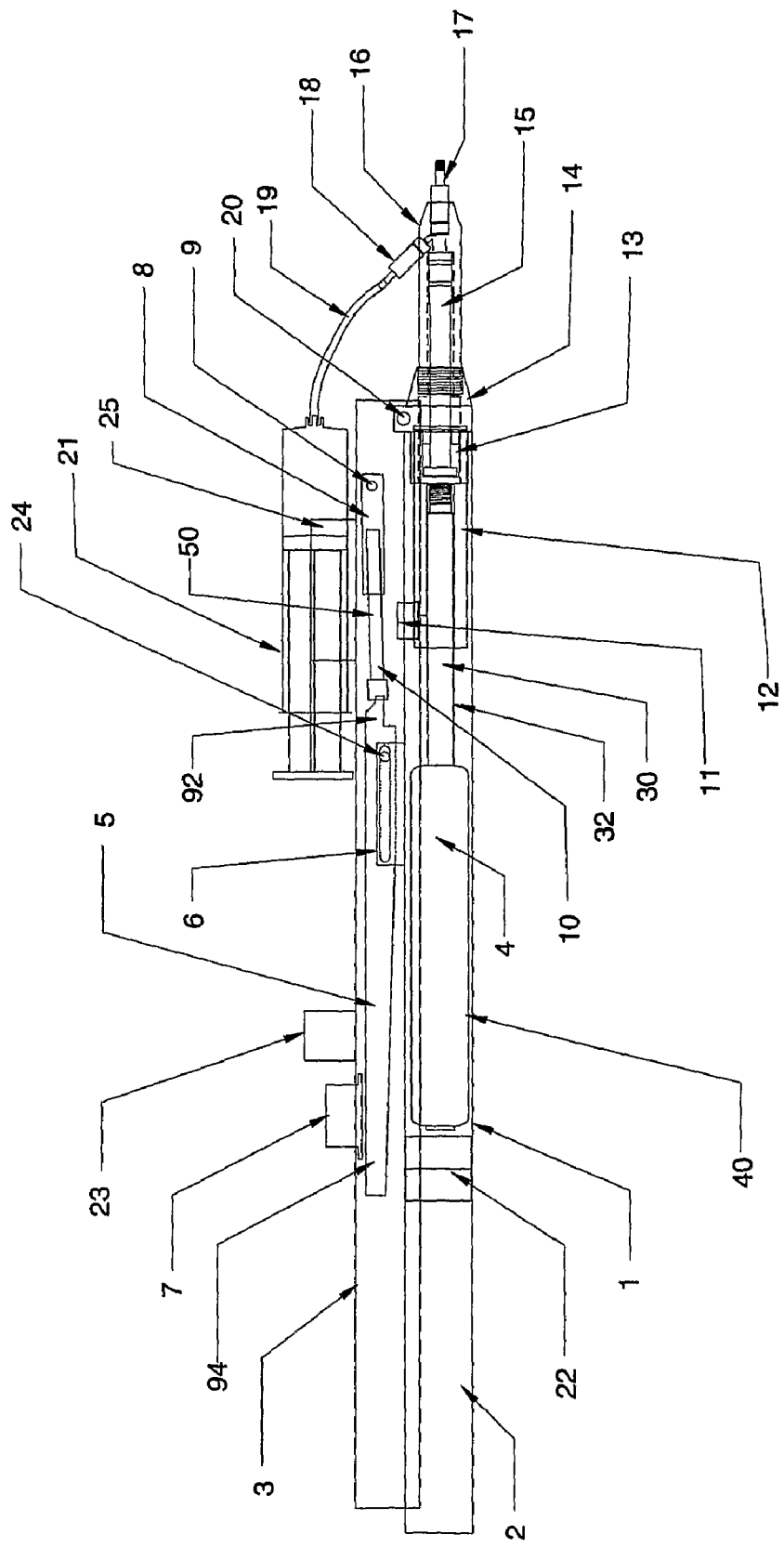
FIG. 2 is a cross-sectional view of a needle-free injection device according to one embodiment of the present invention.
Figure 3:
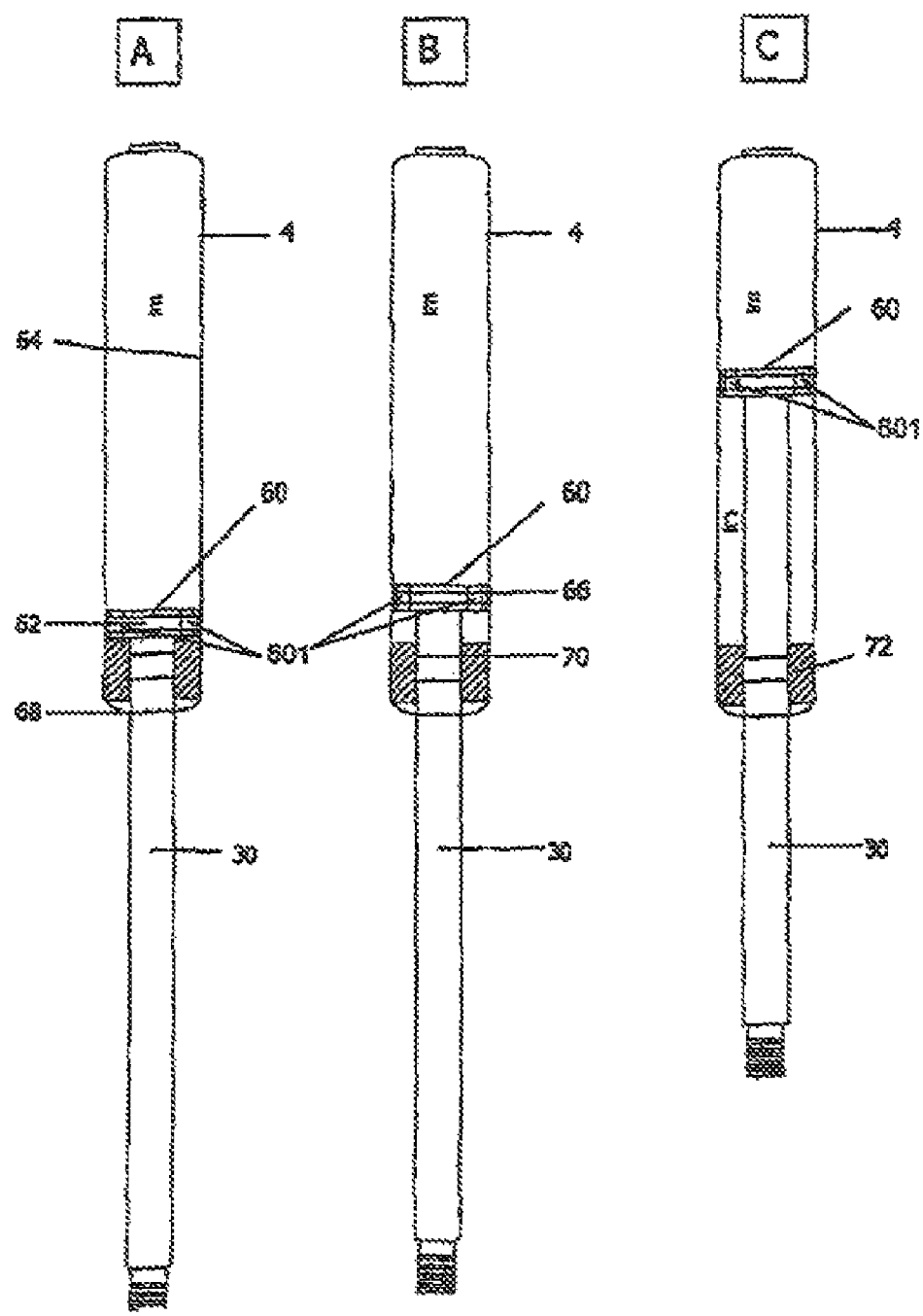
FIG. 3 provides three cross-sectional views of an actuation device in three stages of operation of a needle-free injection device according to one embodiment of the present invention.
Figure 4:
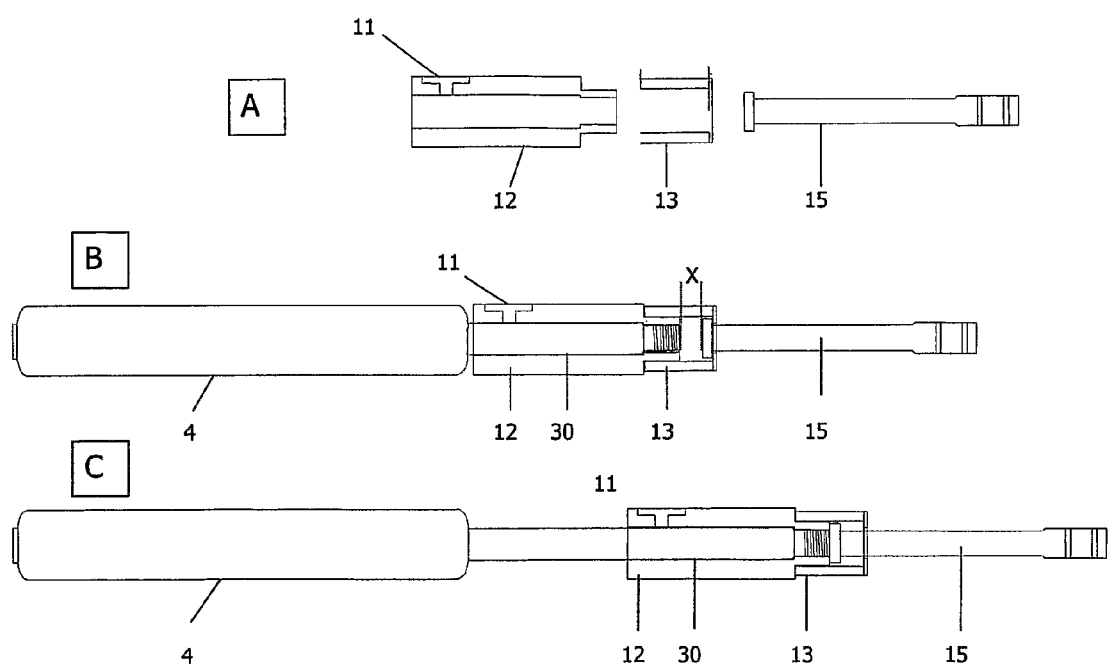
FIG. 4 is a cross-sectional view of a gap-coupling suitable for use in a needle-free injection device according to one embodiment of the present invention.

Generally opposite the discharge end of the dosing reservoir is an expelling means for expelling the liquid within the dosing reservoir through the outlet orifice. In one embodiment of the present invention, as seen in FIG. 2, the expelling means is a plunger 15 slidably received in dosing reservoir 16 and movable between a rearward position and a forward position. Plunger 15 is sized to fit within dosing reservoir 16 such that when it is moved from the rearward position to the forward position it causes the liquid within dosing reservoir 16 to be expelled. Movement of plunger 15 from the rearward to the forward position is controlled by actuating device 40.

Actuating device 40 is disposed within a housing 1 of the needle-free injection device. Components of actuating device 40 are typically formed of a durable material, non-limiting examples of which include, steel, stainless steel and/or an alloy. Components of the needle-free injection device are typically formed of a durable material, non-limiting examples of which include, steel, stainless steel, an alloy, carbon fiber and/or composite plastic.

In accordance with one embodiment of this invention, housing 1 is adapted to be hand-held by a user, and is optionally adapted to receive an extension handle 2 via connector 22. Alternatively, actuating device 40 may be disposed on housing 1. Dosing reservoir 16 is optionally removably attached to housing 1, for example, via a screw fit.

In an alternative embodiment, housing 1 is not configured to hand-held by a user but rather to be attached to a belt or held in a backpack, or the like, which is worn by the user. Alternatively, housing 1 is adapted to be removably attached to a structure. In each case, actuating device 40 remains operatively associated with the dosing portion of the needle-free injection device when in use.

Actuating device 40 comprises a gas tight chamber 4 with a piston and rod assembly 32 reciprocally disposed within chamber 4 and moveable between a forward position and a rearward position. The term "gas tight chamber", as used herein, generally refers to a chamber having a piston and rod assembly reciprocally disposed therein. The gas tight chamber is adapted to minimize or prevent the escape of a pressurized gas, or mixture of gasses, so as to maintain the gas, or mixture of gasses, contained therein in a pressurized state.

Piston and rod assembly 32 includes piston portion 60 and rod portion 30. The shape of piston 60 generally corresponds to the shape of the interior of gas tight chamber 4. In a specific embodiment of the present invention, as depicted in FIGS. 3A, 3B and 3C, the gas tight chamber 4 is substantially cylindrical having an interior with a generally circular cross-section. Piston 60 of piston and rod assembly 32 is generally disk-shaped and the circumference of piston 60 defines an outer edge 62 that is in contact with the interior surface 64 of gas tight chamber 4 such that piston 60 defines an extension portion E and a compression portion C within gas tight chamber 4. The circumference of piston 60 may be defined by sealing member 66, which may be an o-ring. Piston 60 further comprises a through passage 601 for fluid communication between extension portion E and compression portion C. The passage is sized to enable rapid movement of piston and rod assembly 32 within chamber 4 from the rearward position to the forward position. This configuration is similar to that observed in conventional gas-charged springs or shock absorbers, wherein a passage(s) within the piston is sized to dampen or reduce the travel of the piston and rod assembly within the chamber.

In one embodiment, piston 60 has a generally circular passage therethrough having a diameter that is approximately one third (a ratio of 1:3) of the diameter of piston 60. The skilled worker will appreciate that the ratio of the diameter of the circular passage to the diameter of the piston 60 can be varied. If, for example, the ratio is 1:6, thereby having a smaller passage diameter as compared to the ratio of 1:3 mentioned above, the speed of the piston and rod assembly 32 would be decreased. This decrease in speed would allow for the use of a gas-charge, which would otherwise be used for a larger animal or humans, for injecting a smaller sized animal or human. In contrast, as the ratio approaches 1:1, the speed of piston and rod assembly 32 would be increased, as compared to the ratio of 1:3 mentioned above. In such a 1:1 configuration, gas-tight chamber 4 is constructed of sufficiently strong material to ensure piston and rod assembly 32 does not breach the end of the chamber 4 when moving to the forward position.

Rod 30 of piston and rod assembly 32 is disposed within chamber 4 and through opening 68 in chamber 4. Interaction of rod 30 with sealing means 70 positioned about opening 68 of chamber 4 provides a seal so as to minimize or prevent escape of the gas charge from chamber 4. In a specific embodiment, sealing means 70 is an o-ring.

In accordance with another embodiment of the invention, chamber 4 is provided with reinforcing members 72 positioned adjacent to opening 68. Reinforcing members 72 act to provide support to the walls of chamber 4 and to rod 30.

Chamber 4 contains a gas charge for urging piston and rod assembly 32 to its forward position (as shown in FIG. 3A). The term "gas charge", as used herein, generally refers to a pressurized inert gas, or a pressurized mixture of more than one type of inert gas, contained within gas tight chamber 4. Examples of inert gases suitable for use in the actuating device of the needle-free injection device of the present invention include, but are not limited to, nitrogen, carbon dioxide, helium, neon, argon, krypton, xenon, and mixtures thereof. Selection of the inert gas will depend on various factors, including: the application, cost, ease of use etc. In practice, empirical tests can be used to confirm the suitability of a selected gas or gas mixture. In such tests, the suitability can be determined by measuring the depth of injection achieved in comparison to the depth when injection is performed with a traditional needle (an industry standard) and/or the recommended depth of medicament placement by medicament manufacturers. Advantageously, the inert gas is nitrogen. Conventional means of introducing a gas charge into chamber 4 can be used and are know to the skilled worker.

The pressure of the gas charge within gas tight chamber 4 is greater than that of the surrounding atmospheric pressure, thus urging piston and rod assembly 32 to the forward position (as shown in FIG. 3A). Ultimately, selection of the appropriate gas pressure and type of gas will depend on the application of the injection device. Advantageously, the pressure of the gas charge within the gas tight chamber is selected such that the medicament is expelled with a force of from 100 N to 5000 N. As with certain currently used needle-free injection devices, the generated force can be adjusted, for example, by increments of 50 N (e.g., 100 N, 150 N, 200 N . . . 4550 N, 5000 N). However, it will be clear to the skilled worker that any force between 100 N and 5000 N can be selected depending on the force required to pierce the skin of the subject. The force can be adjusted by adjusting the pressure of the gas charge.

As piston and rod assembly 32 is moved from the forward position to the rearward position, the pressure of the gas acting to urge piston and rod assembly 32 forward increases. The repulsive force of the compressed gas on piston and rod assembly 32 is related to the pressure of the gas charge and the surface area of piston and rod assembly 32 exposed to the compressed gas.

In accordance with an embodiment of the present invention an actuating device 40 includes a lubricating medium for lubricating the interaction of piston and rod assembly 32 and the interior of chamber 4. The lubricating medium may also enhance the sealing interaction between rod 30 of piston and rod assembly 32 and o-ring 66 in opening 68 of chamber 4. The loss of the gas charge and/or lubricating medium from chamber 4 is minimized or prevented due to the sealing interaction of rod 30 and sealing member 70. It will be appreciated by those skilled in the art that nature of the lubricating medium, if present, depends on the overall application of the actuating device 40, and the conditions in which it is used. In one example, the volume and viscosity of the lubricating medium is selected such that the movement of piston and rod assembly 32 from the rearward position to the forward position within gas-tight chamber 4 is not significantly dampened by the presence of the lubricating medium. For example, a small volume of light weight oil is less likely to dampen the travel of the piston and rod assembly 32 than a larger volume or a heavier weight oil. In contrast, if the skilled user requires that the velocity of piston and rod assembly 32 be dampened (which may be necessary if, for example, a high pressure gas-charge is to be used), a greater volume or more viscous oil is used.

When the actuation device is installed in a needle-free injection device, the piston and rod assembly may be slightly compressed, as shown in FIG. 3B. This slight compression aids in distribution of the lubrication medium around piston and rod assembly 32.

In one embodiment of the present invention, the actuating portion and the dosing portion of the injection device are directly attached to one another. In this embodiment, gap-coupling 13 connects piston 30 of piston and rod assembly 32 to plunger 15. Gap-coupling 13 maintains a gap-distance X between rod 30 and plunger 15 when piston and rod assembly 32 is in the rearward position. Gap-coupling 13 is removably attached to rod 30 and is in sliding engagement with plunger 15. As depicted in FIGS. 4A, 4B and 4C, plunger 15 is fitted through an opening in gap-coupling 13, such that plunger 15 is slidingly received within one end of gap-coupling 13. Gap-coupling 13 is attached at the opposite end to connector 12, which is, in turn, connected to rod 30. In an alternative embodiment, gap-coupling 13 is attached directly to piston and rod assembly 32 and no connector is required. It will be apparent to the skilled worked that gap-coupling 13 can be connected to rod 30 and plunger 15 in a variety of ways, provided that the gap-distance X is maintained between piston and rod assembly 32 and plunger 15 when piston and rod assembly 32 is in the rearward position. This configuration results in "direct" impact of plunger 15 by piston and rod assembly 32 when it is released for movement by said gas charge to its forward position.

Figure 8:
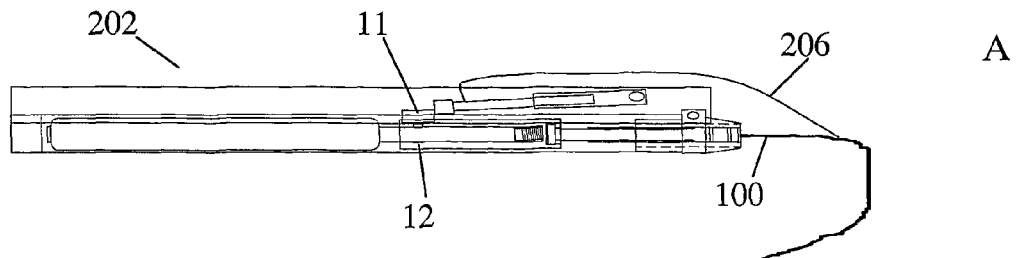
FIGS. 8 A and B are cross-sectional views of a needle-free injection device (A) and a hand-held unit (B) according to one embodiment of the present invention.
Figure 8:
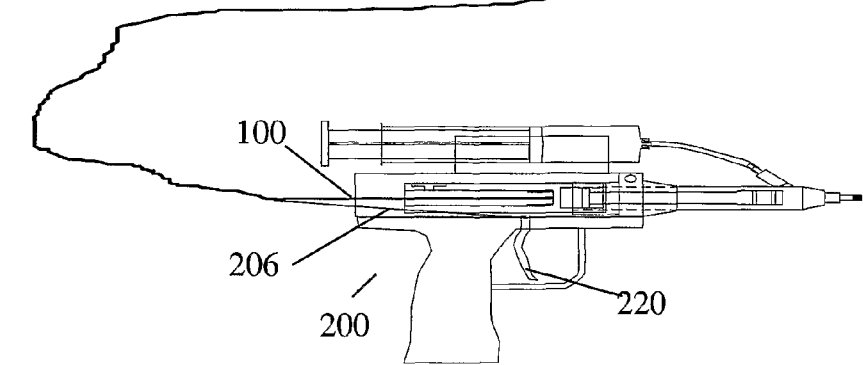
Figure 8:
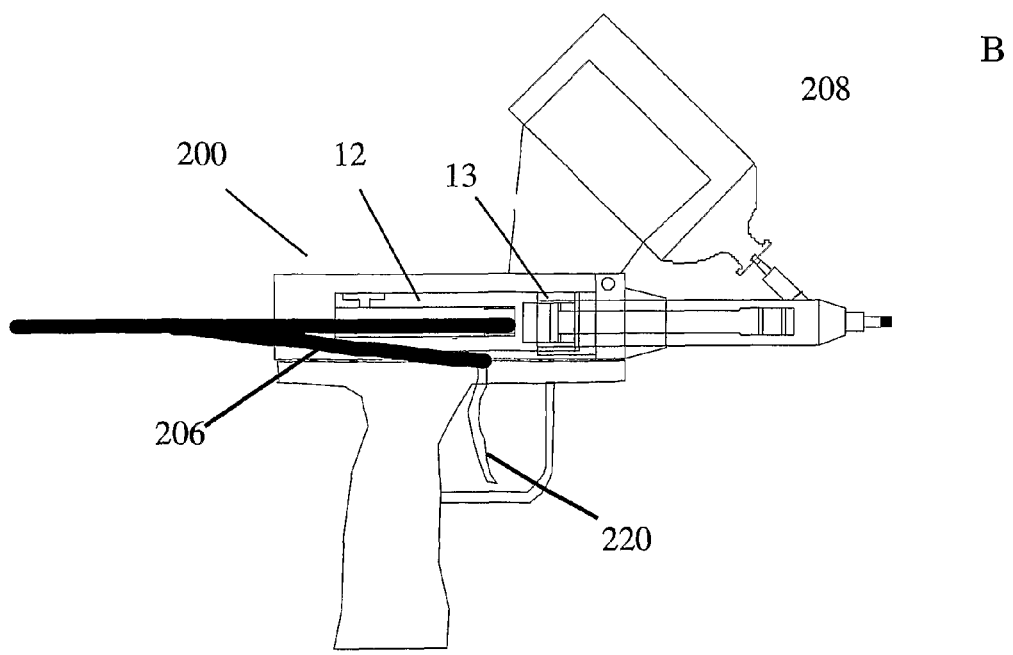
Figure 9:
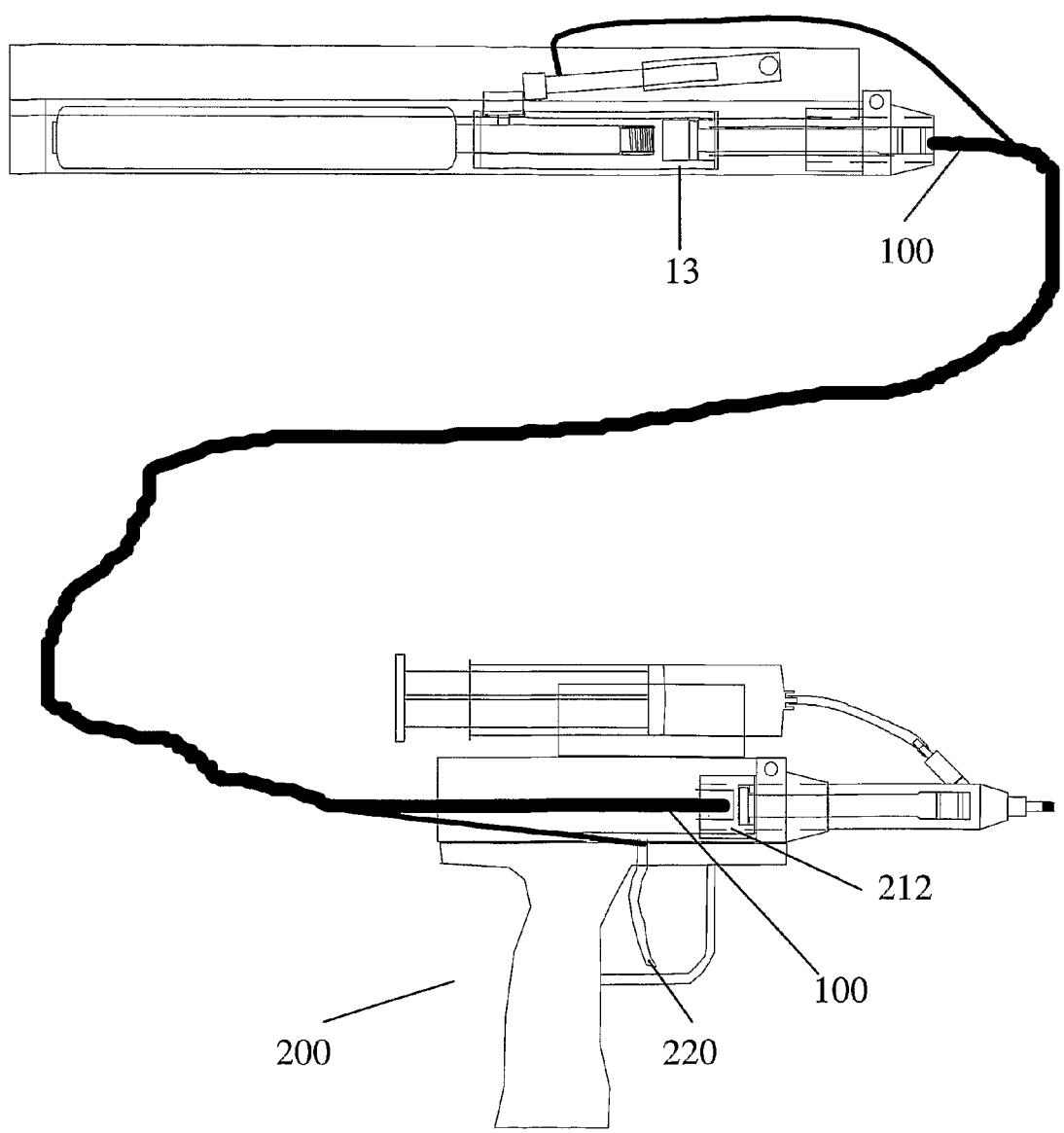
FIG. 9 is a cross-sectional view of a needle-free injection device according to one embodiment of the present invention.
Figure 10:
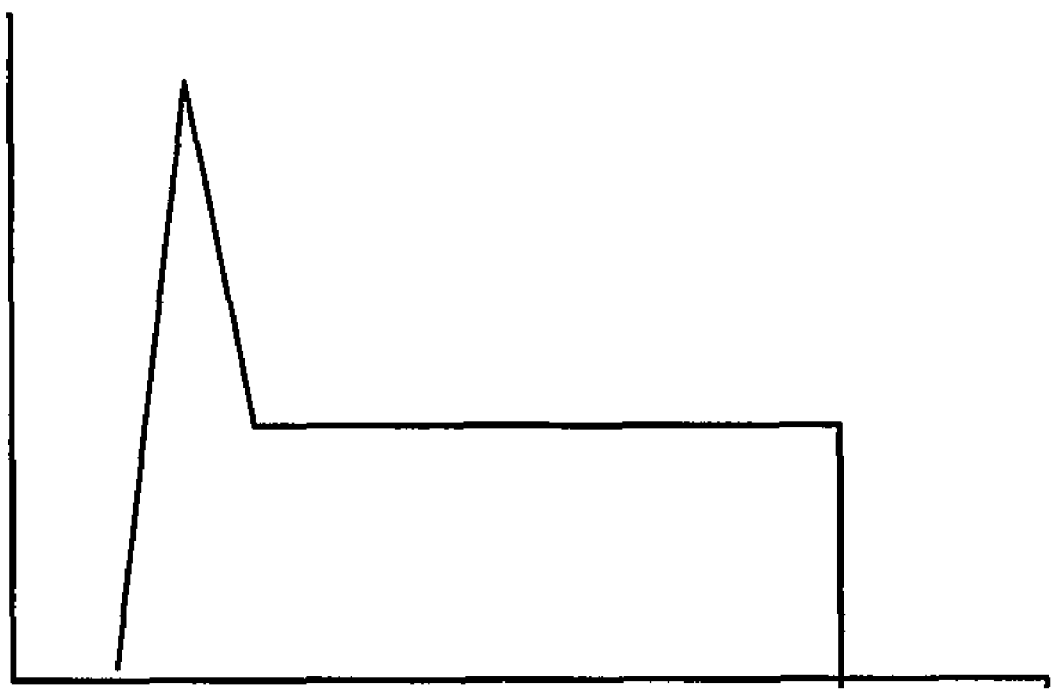
FIG. 10 is a graphical representation of the pressure pattern observed after triggering the injection device of the present invention.
Figure 11:
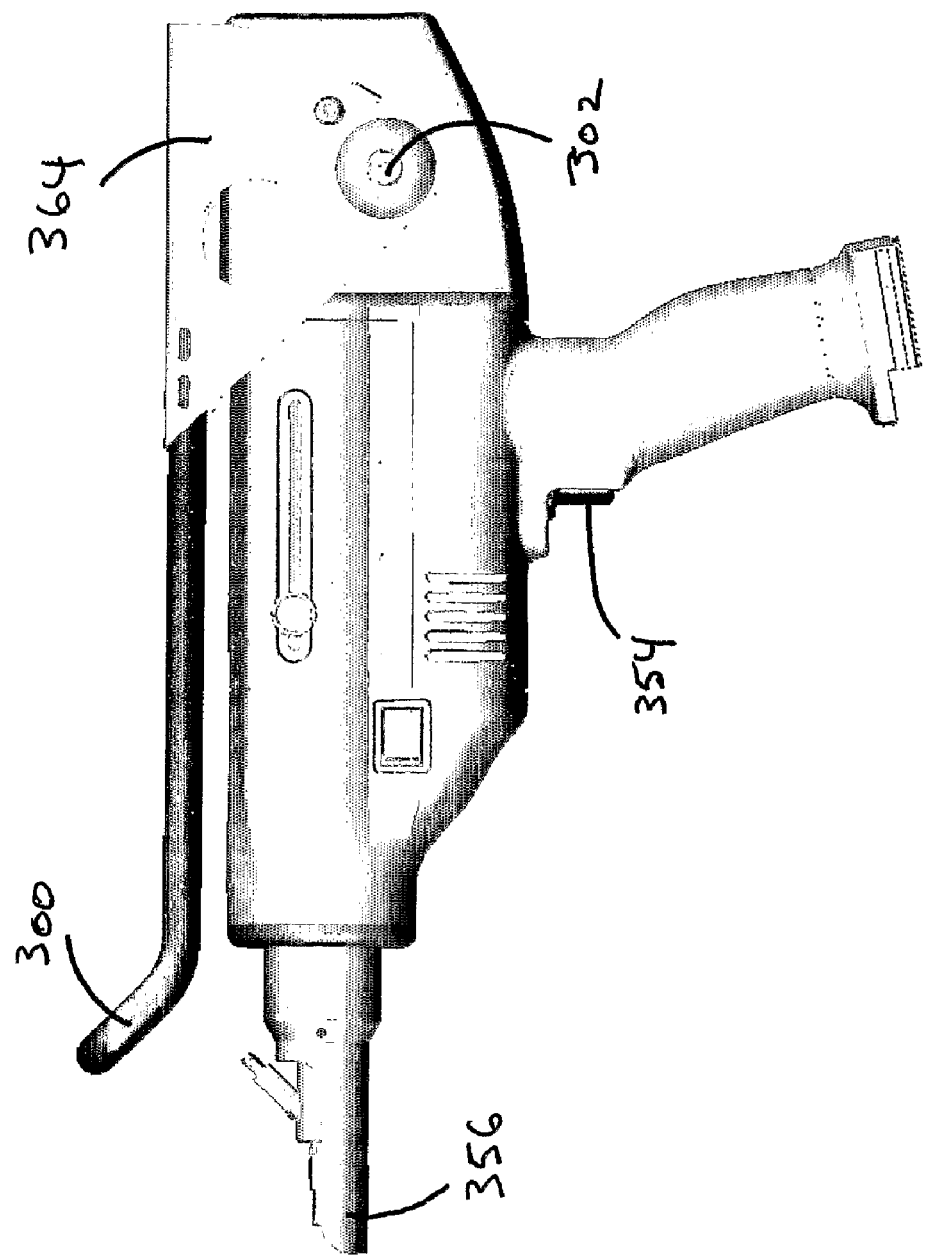
FIG. 11 is a side view of one embodiment of the needle-free injector of the present invention.
Figure 12:
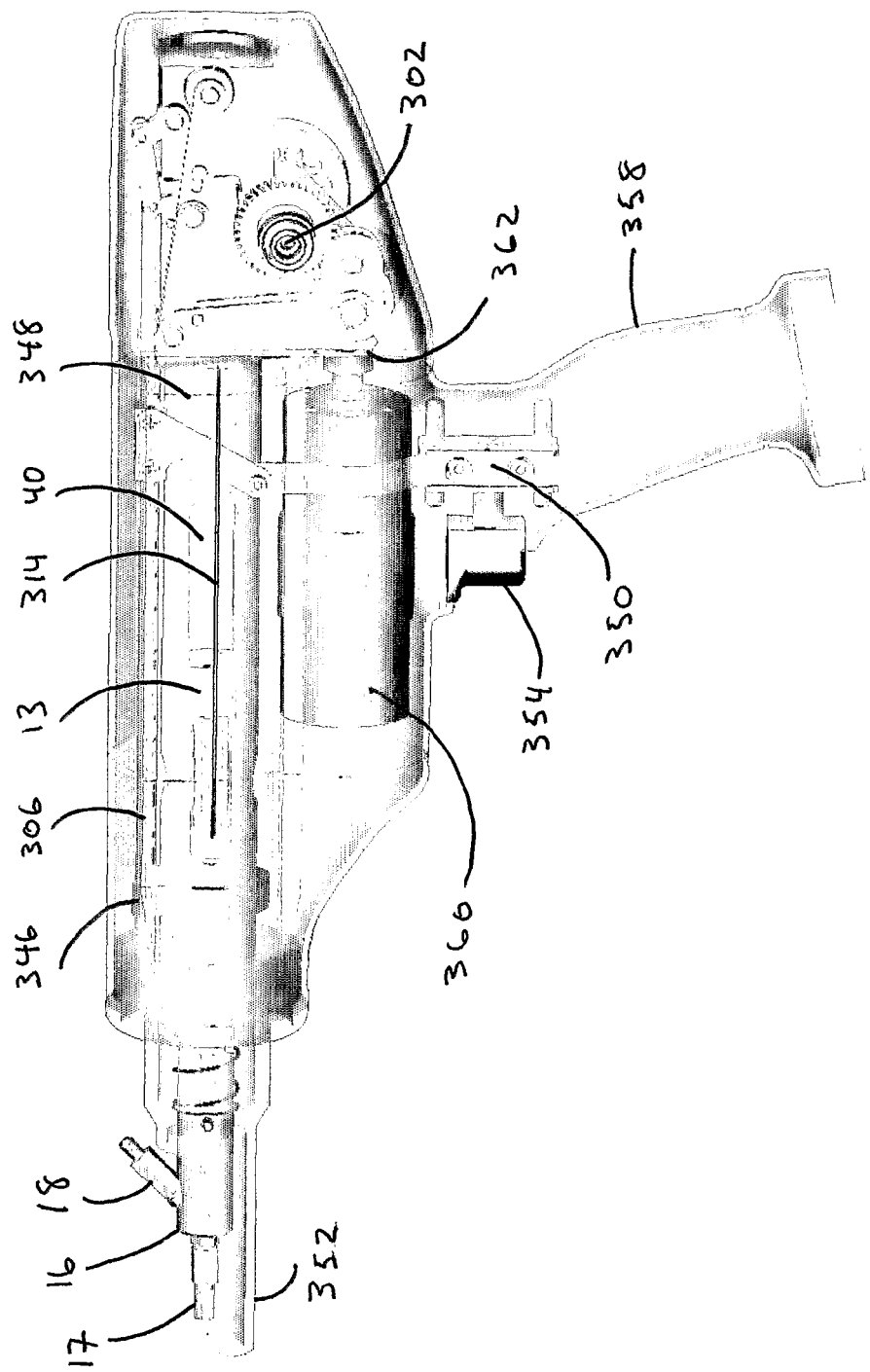
FIG. 12 is a cross-section side view of the needle-free injection device depicted in FIG. 11.
Figure 13:
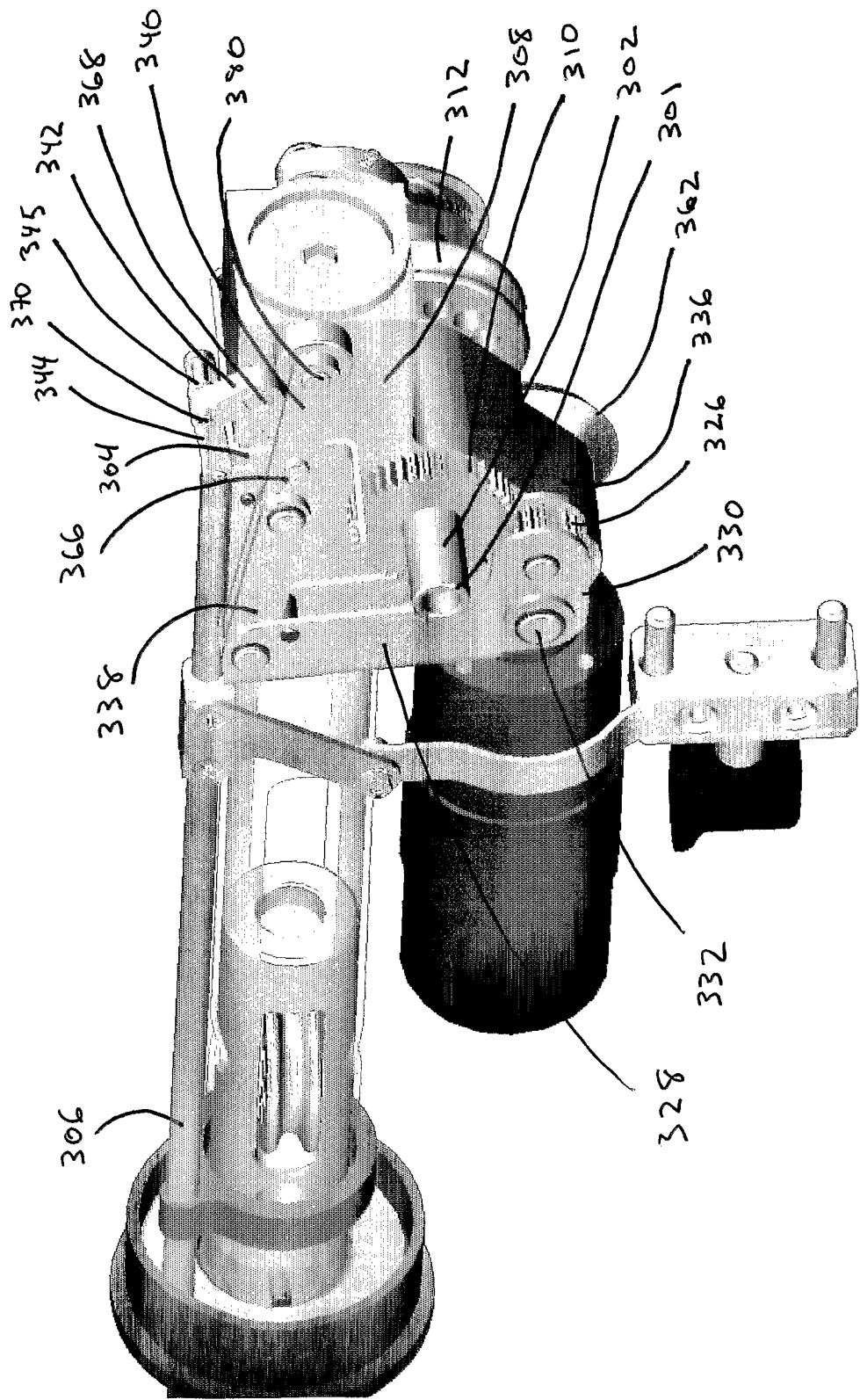
FIG. 13 is a partial perspective view of the needle-free injection device depicted in FIG. 11.
Figure 14:
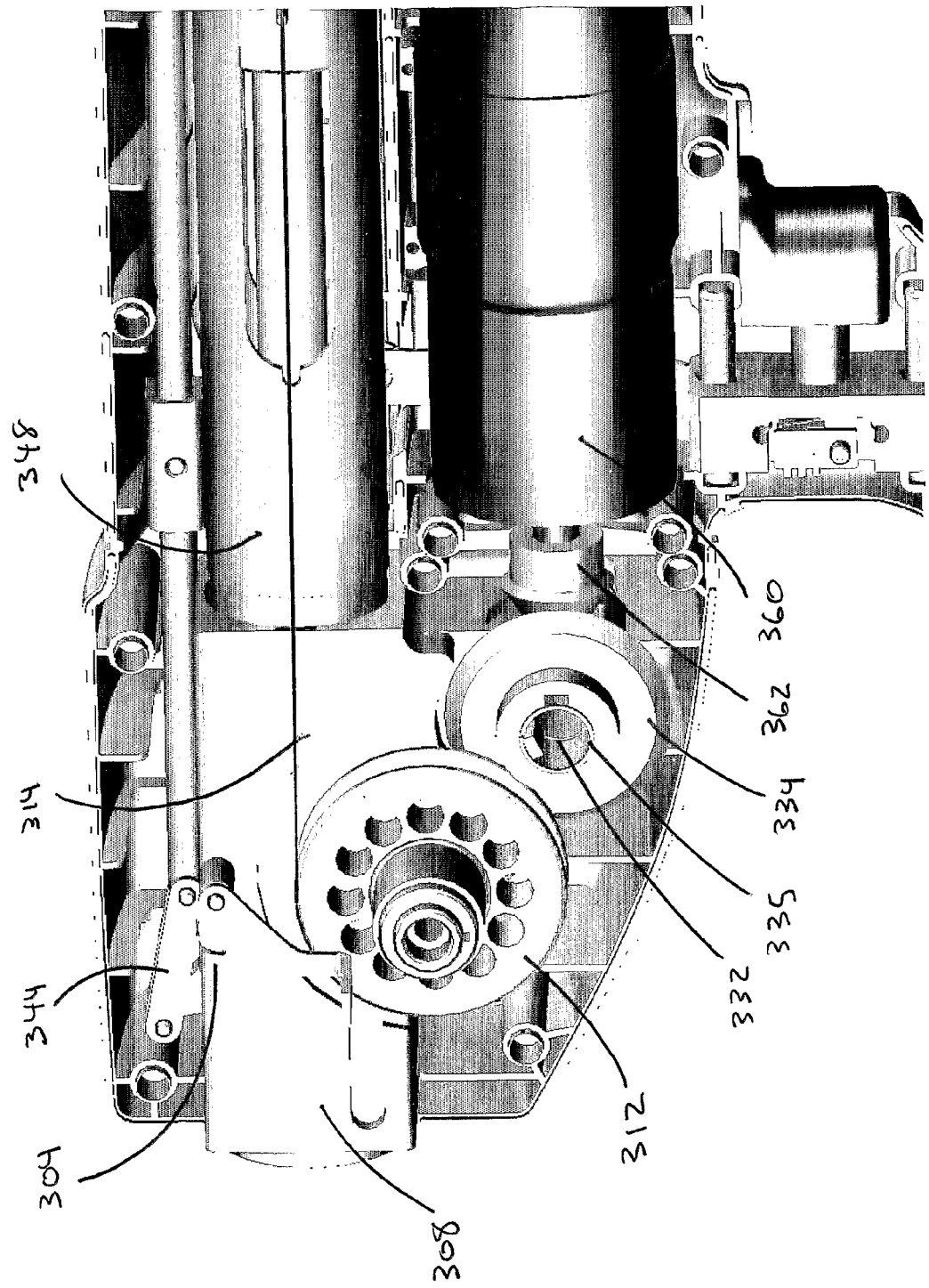
FIG. 14 is a partial perspective view of the needle-free injection device depicted in FIG. 11.
Figure 15:
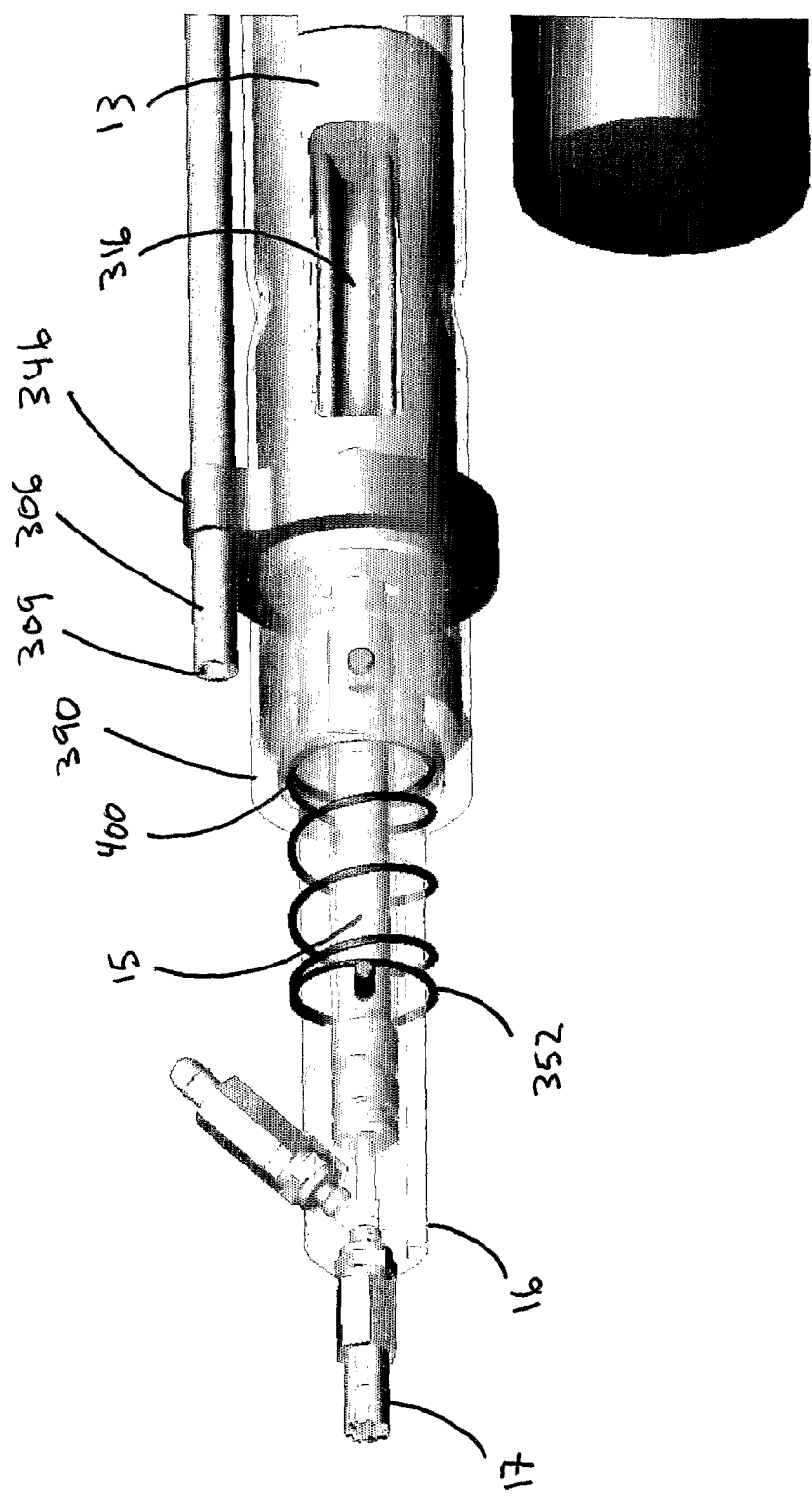
FIG. 15 is a partial perspective view of the needle-free injection device depicted in FIG. 11.
Figure 16:
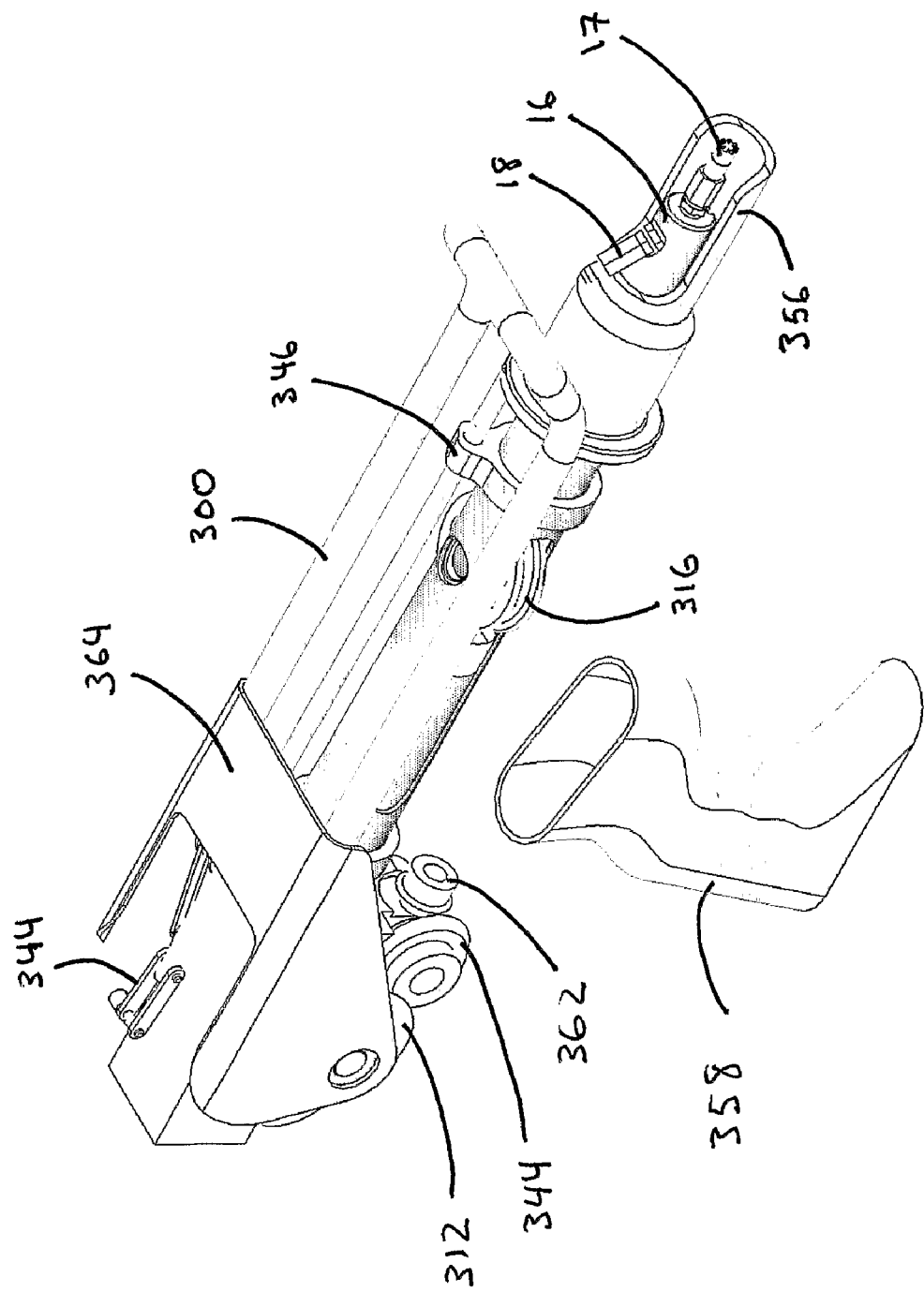
FIG. 16 is a perspective, partially exploded view, of the needle-free injection device depicted in FIG. 11.
Figure 17:
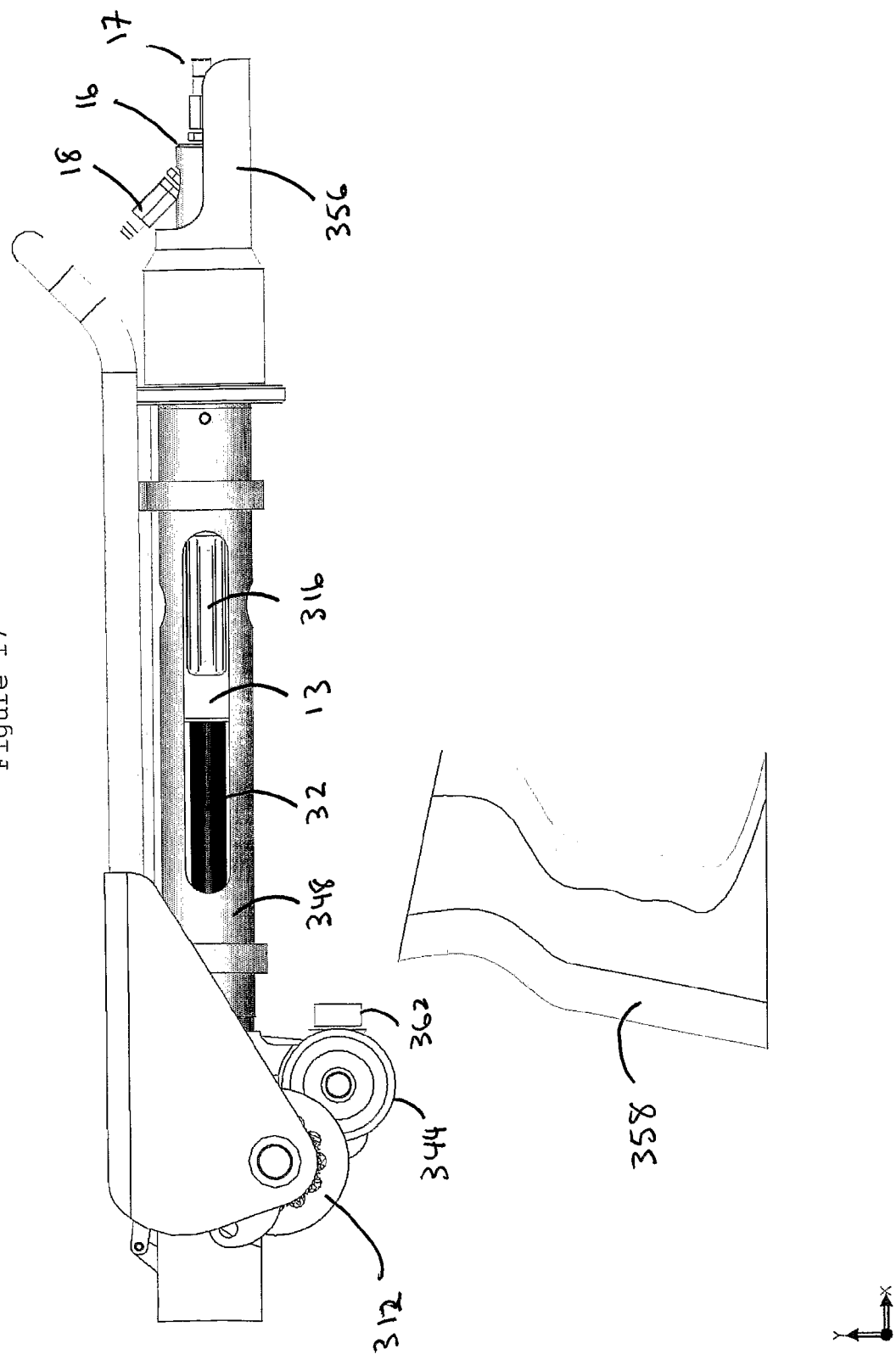
FIG. 17 is a side, partially exploded view, of the needle-free injection device depicted in FIG. 11.
Figure 18:
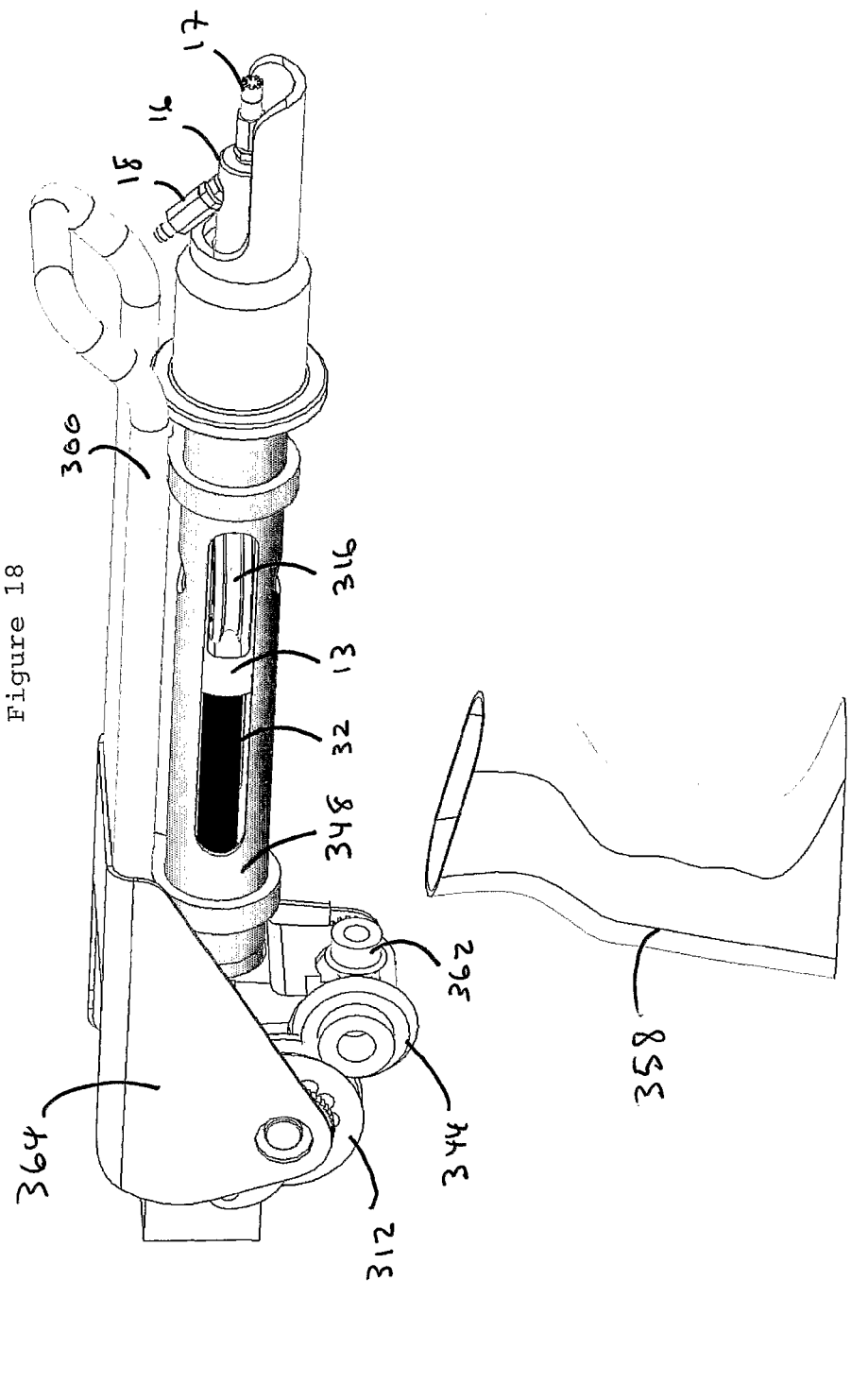
FIG. 18 is a perspective, partially exploded view, of the needle-free injection device depicted in FIG. 11.
Figure 19:
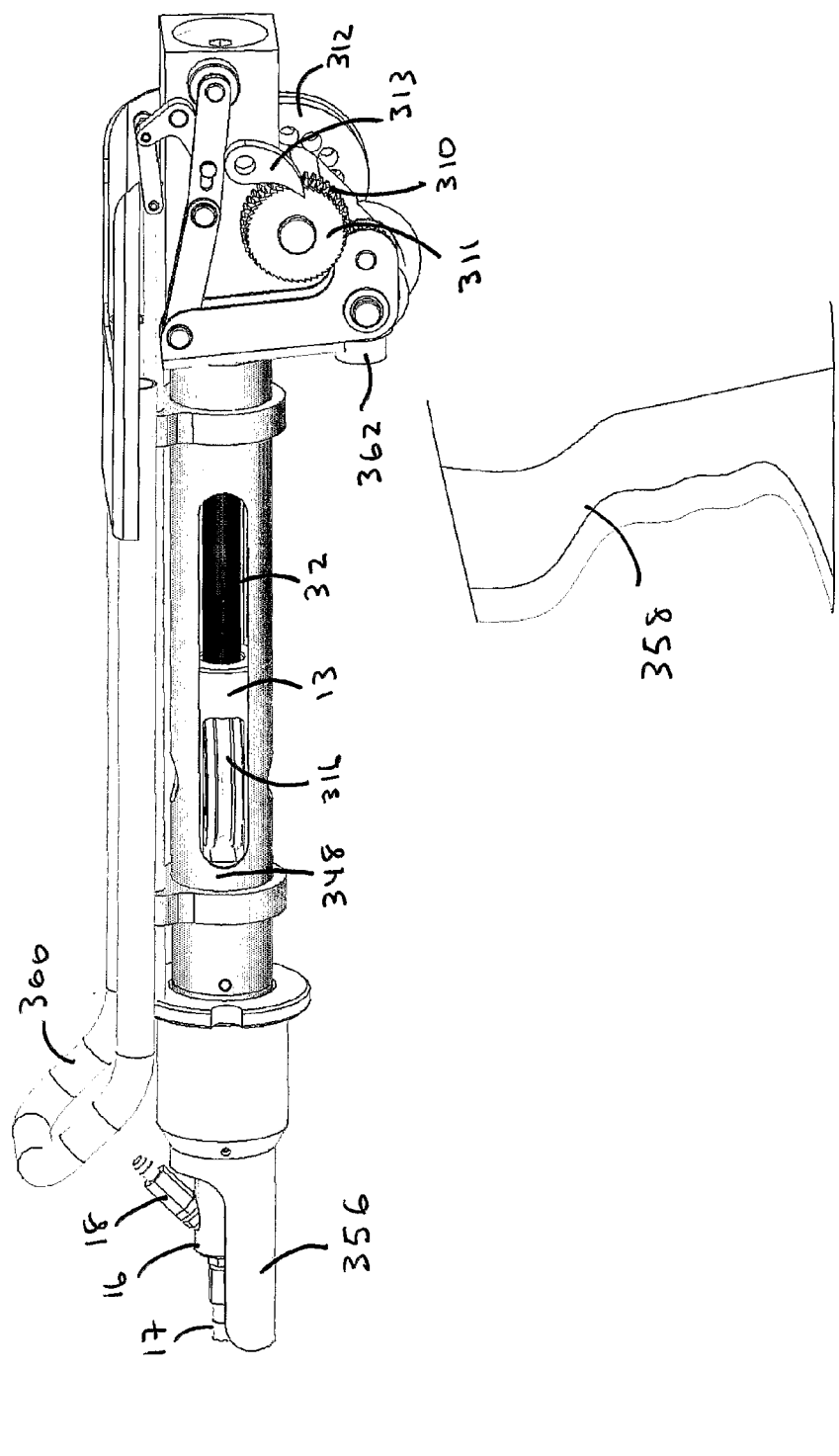
FIG. 19 is a side, partially exploded view, of the needle-free injection device depicted in FIG. 11.
Figure 20:
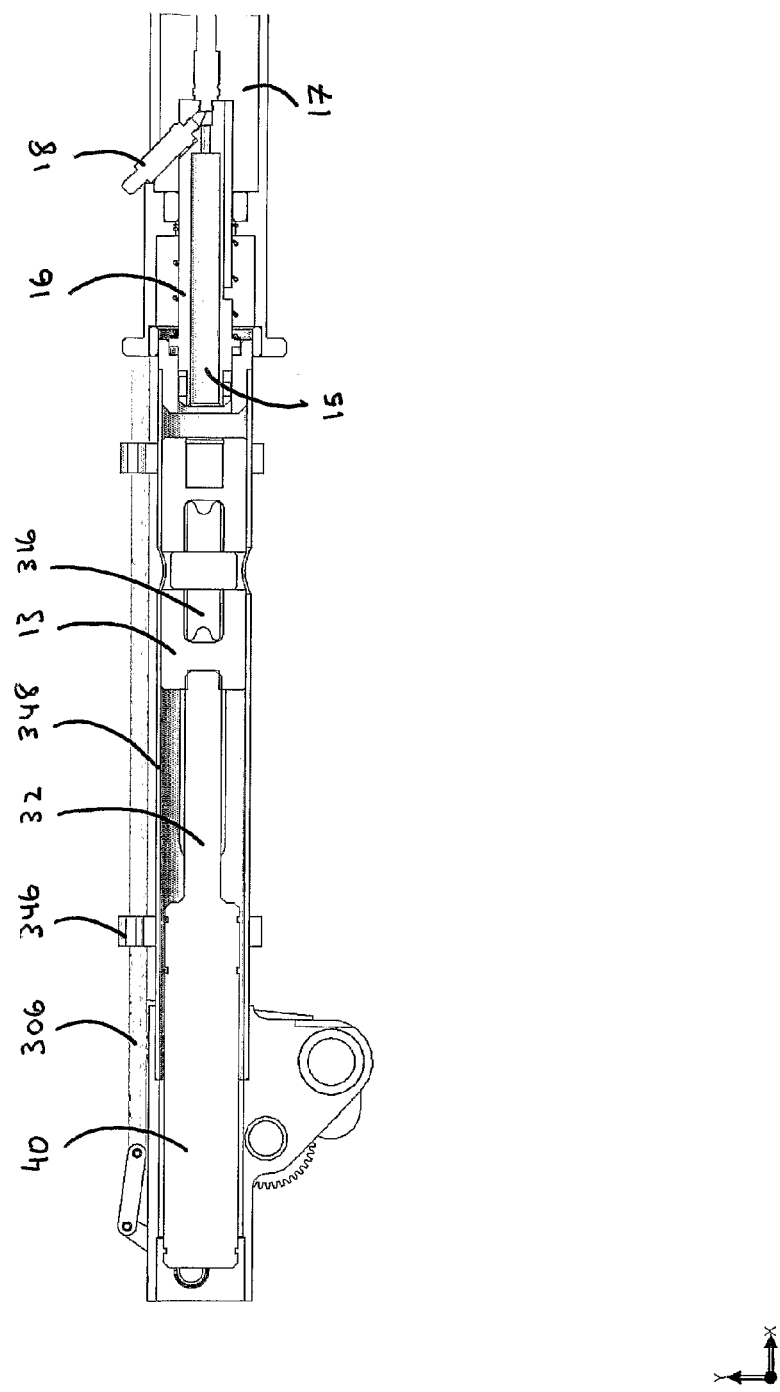
FIG. 20 is a longitudinal cross sectional view of the needle-free injection device depicted in FIG. 11.
Figure 21:
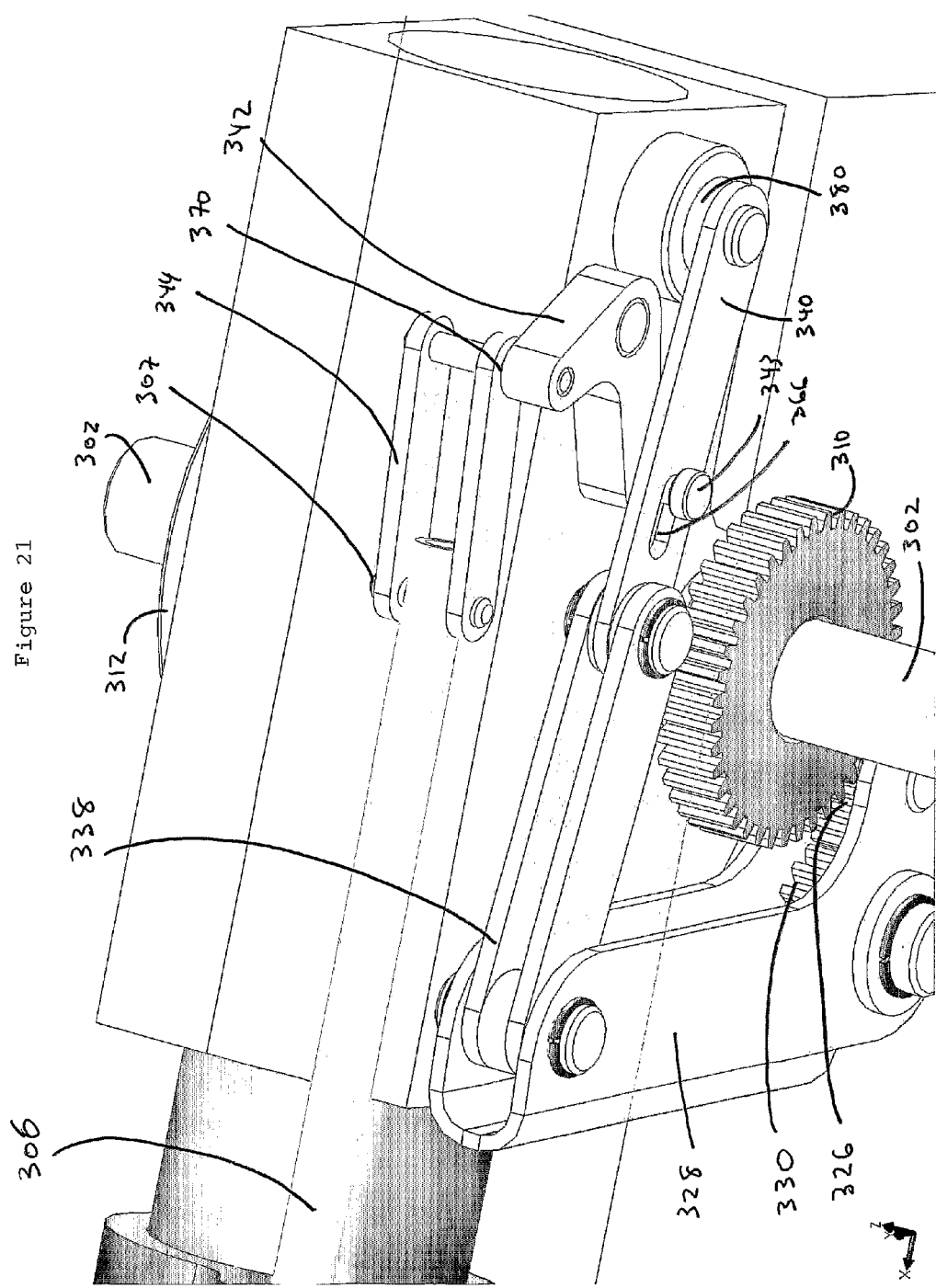
FIG. 21 is a partial perspective view of the needle-free injection device depicted in FIG. 11.

In some instances, it may be desirable for the actuating portion of the injection device to be located apart from the dosing portion (see FIGS. 8 and 9). This can be advantageous, for example, if the actuating device is heavy and, therefore, it is easier for a user to carry the actuating portion at their waist, back, slung over a shoulder, or the like, in a remote portion 202. In this embodiment, hand-held portion 200 contains dosing chamber 16, plunger 15 and nozzle 17. In such a configuration of the needle-free injection device, transferring means 100 for transferring force generated by movement of piston and rod assembly 32 to said plunger 15 is incorporated into the overall device. This configuration results in "indirect" impact of plunger 15 by piston and rod assembly 32 when it is released for movement by said gas charge to its forward position. Specifically, activation of the trigger causes piston and rod assembly 32 to be released for movement by said gas charge to the forward position thereby imparting a force to transferring means 100, which in turn transfers the force to plunger 15. In such an example, gap-coupling 13 connects transferring means 100 to plunger 15 (FIG. 8), or piston 30 of piston and rod assembly 32 to transferring means 100 (FIG. 9). Gap-coupling 13 maintains gap-distance X between transferring means 100 and plunger 15 (FIG. 8), or between piston 30 and transferring means 100 (FIG. 9), respectively, when piston and rod assembly 32 is in the rearward position. Transferring means 100 can be in the form of, for example, a closed hydraulic hose, a flexible multi-link cable/shaft enclosed in a casing, or the like.

The appropriate gap-distance X is selected to maximize the velocity of piston and rod assembly 32 following triggering of the device and before direct or indirect impact with plunger 15. This, in turn, maximizes the available force for impact of the liquid at the orifice end of the device. This impact force is important to the operation of the device, since it provides the opening for the medicament to pass through the skin and the subcutaneous tissue. Gap-distance X also allows the injector to perform injections in large animals using relatively low pressures because the impact required for piercing skin and subcutaneous tissue is far greater than the pressure required to inject the remaining dosage of the medicament into the desired tissue. This makes the injector safer and much less painful to the subject receiving an injection in comparison to conventional needle-free injection devices. To draw a comparison, when triggered, an injector that operates with one constant pressure during an injection pierces the skin and subcutaneous tissue and delivers the liquid to be injected using the same pressure. If the user moves or slides the orifice end of the device during this process the flesh of the subject can be sliced, as with a scalpel, thus potentially causing severe wounds. By including a gap-coupling 13, the pressure is delivered in a spike formation where, at impact, the pressure spikes to the desired level to pierce the tissue, but drops to perform the remainder of the injection (See FIG. 10).

If gap-distance X is too small, piston and rod assembly 32 is unable to reach maximum velocity, the impact is lessened and the force at the orifice available for piercing is less. If the gap-distance X is increased, very little effect on impact pressure results due to the fact that the maximum velocity has already been reached and therefore maximum force had been reached at the orifice end.

In one embodiment of the present invention, gap-distance X is a fixed distance. In one example the gap-distance is ⅜ inch. In an alternative embodiment, the gap-coupling is user adjustable such that the gap-distance can be varied depending on the application of the device. In another alternative embodiment, the gap-coupling is integral to rod 30.

In operation, as piston and rod assembly 32 moves from the rearward position to the forward position it travels gap-distance X before the impact end of rod 30 impacts, either directly (FIGS. 2, 4 and 5) or indirectly, via transferring means 100 (FIGS. 8 and 9), the rear end of plunger 15. Plunger 15, in turn, moves from its rearward position to its forward position within dosing reservoir 16 so as to expel a liquid from dosing reservoir 16 through nozzle 17.

Actuating device 40 of the needle-free injection device of the present invention further comprises means for moving piston and rod assembly 32, against the gas charge in gas tight chamber 4, from its forward to its rearward position. Through use of this means for moving, a user is able to "charge" the injection device in order to make it ready for injection. The means for moving piston and rod assembly 32 may be a motorized or manual means.

In accordance with a specific embodiment of the present invention the means for moving piston and rod assembly 32 are motorized means. Such motorized means may include DC (optionally rechargeable) and/or AC power supplies. In one example, the motor will be removably mounted on its own assembly or within a bracket.

Figure 5:
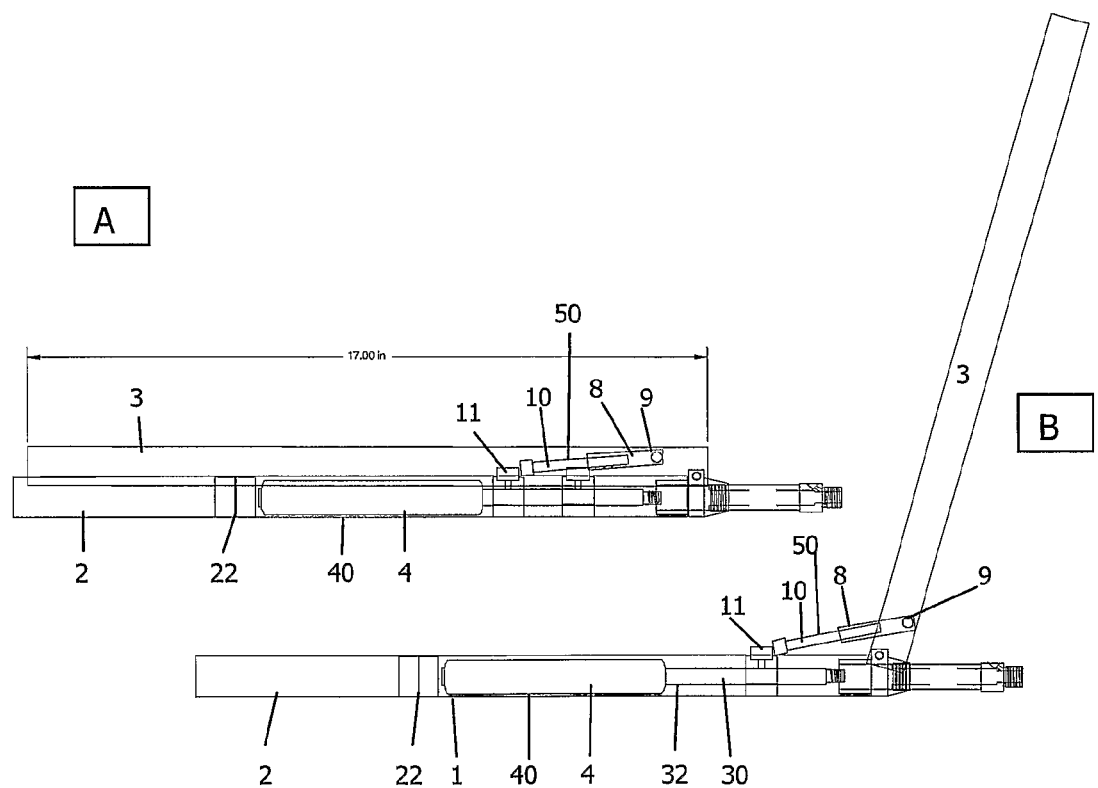
FIG. 5 is a cross-sectional view of a manual means for moving the piston and rod assembly against the gas charge in a needle-free injection device according to one embodiment of the present invention.
Figure 6:
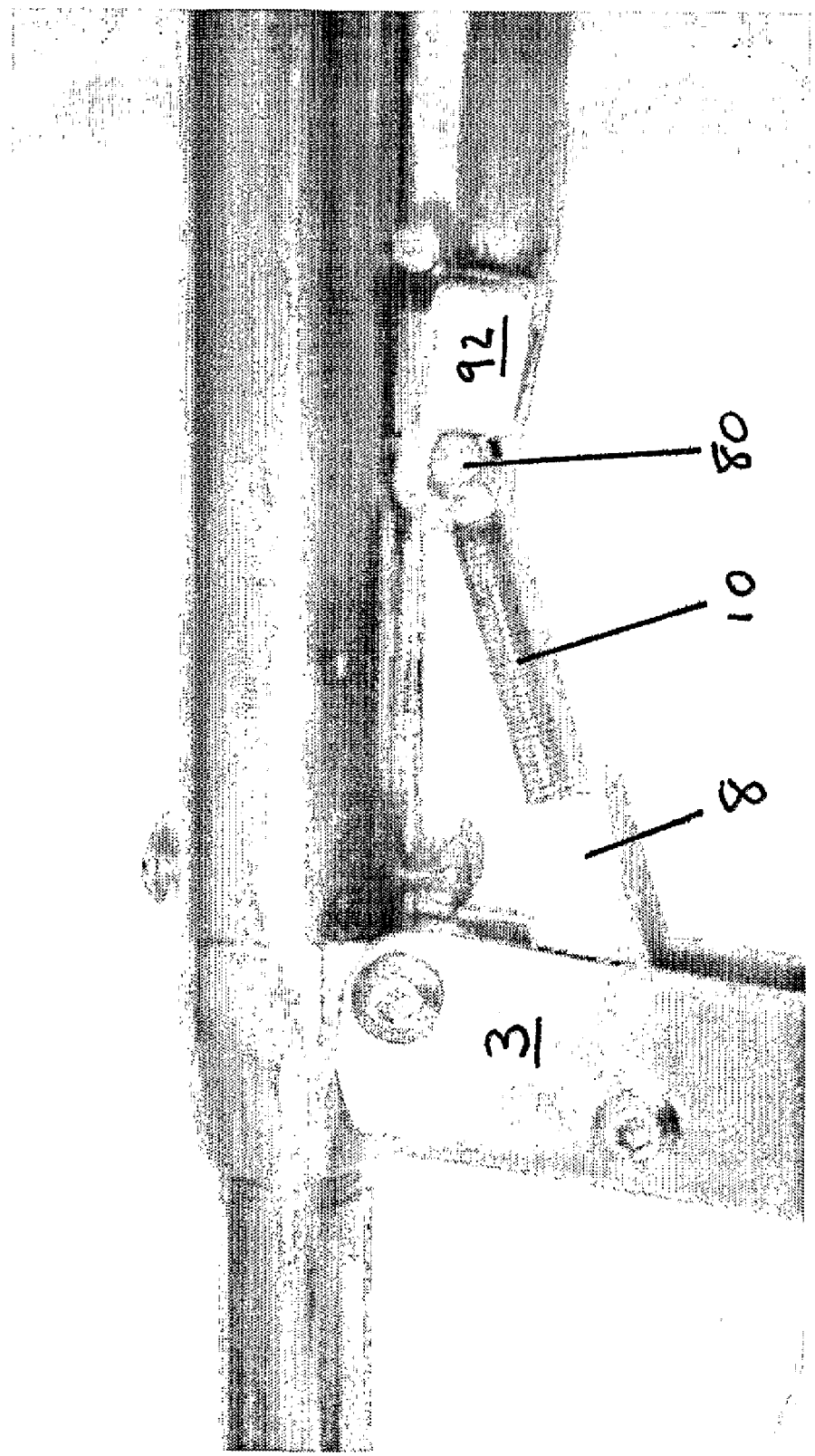
FIG. 6 is a photograph of an example of the manual charger depicted in FIG. 5.
Figure 7:
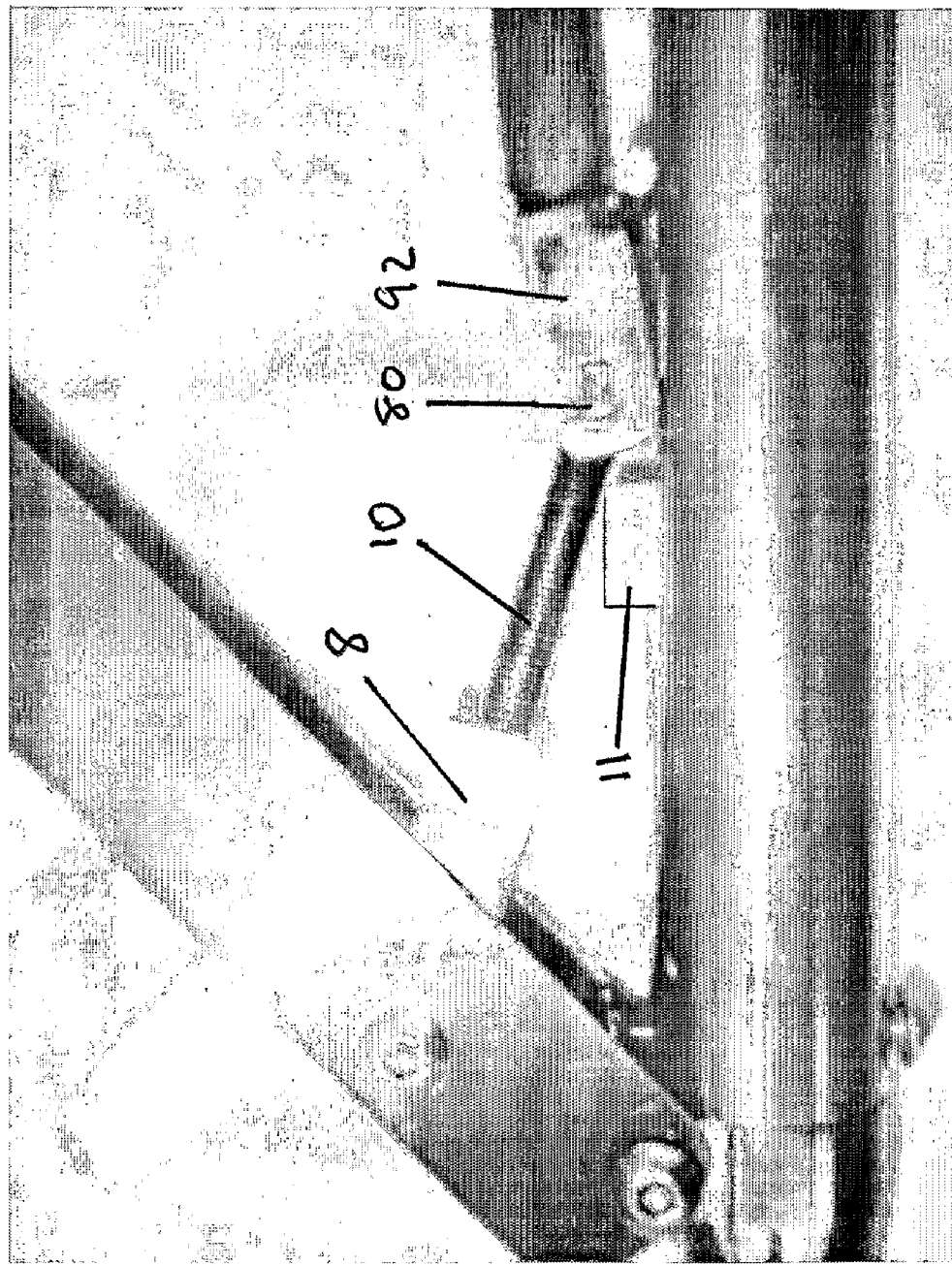
FIG. 7 is a photograph of an example of the manual charger depicted in FIG. 5.

In accordance with an alternative embodiment of the present invention the means for moving piston and rod assembly 32 are manual means. One example of such manual means is depicted in FIG. 5. Handle 3 is pivotally connected to housing 1 of the needle-free injection device and is pivotable from a first, closed position (as shown in FIG. 5A) to a second, open position (as shown in FIG. 5B). Push rod 50 is pivotally attached to handle 3. Push rod 50 can be fixed in length or can be configured to allow a variation in length. For example, push rod 50 depicted in FIG. 5, includes a threaded member 10 received within a thread receiving body 8. The length of push rod 50 is decreased or increased by threading or unthreading, respectively, threaded member 10 within receiving body 8.

FIGS. 8 and 9 depict an injection device of the present invention comprising a remote portion 202 that is distantly related from hand-held portion 200. In accordance with this embodiment of the present invention the means for moving piston and rod assembly 32 is a motorized or a manual means, as described above. Furthermore, the motorized or manual means can be attached to either remote portion 202 or hand-held portion 200.

In operation, movement of handle 3 from the first, closed position (FIG. 5A) to the second, open position (FIG. 5B) brings push rod 50 into engagement with actuating member 11. Actuating member 11 is operatively associated with rod 30 of piston and rod assembly 32 such that movement of actuating member 11 causes corresponding movement of piston and rod assembly 32 in order to move it, against the gas-charge, from its forward position to its rearward position. This movement "charges" or actuates the injection device.

In the specific embodiments of the present invention depicted in FIGS. 1, 2, 4, 5, 6, 7 and 9, actuating member 11 is a attached to gap-coupling 13 via connector 12 and connector 12 is removably attached to rod 30. In FIG. 8, actuating member 11 and connector 12 are removably attached to rod 30 and to means for transferring force 100, which is in turn attached to gap-coupling 13 via a second connector 212. Movement of handle 3 from the first, closed position to the second, open position results in the push rod 10 engaging a notch 80 in actuating member 11. Movement of handle 3 from the second, open position back to the first, closed position transfers a pushing force to actuating member 11 which, in turn, moves piston and rod assembly 32, via movement of connector 12, from its forward position to its rearward position. In an alternative embodiment actuating member 11 is directly connected to piston and rod assembly 32.

Once in the rearward position, piston and rod assembly 32 is held in place by a trigger. The trigger is a mechanism that maintains piston and rod assembly 32 in the rearward position and is user activatable to allow piston and rod assembly 32 to be released from its rearward position to move to the forward position due to the pressure generated by the compressed gas-charge.

In accordance with one embodiment of the present invention, user activation of the trigger causes disengagement of push rod 50 from actuating member 11. In the specific embodiment depicted in FIG. 2, the trigger comprises triggering lever 5 having a first end 92 and a second end 94 and being pivotable about pivot member 24. Triggering lever 5 is connected at first end 92 to push rod 50. When a downward force is exerted on second end 94, for example by button 7, triggering lever 5 pivots about pivot member 24 and first end 92 is raised, thus causing push rod 50 to disengage actuating member 11. Once push rod 50 is disengaged from actuating member 11, forward movement of piston and rod assembly 32 is committed, that is, there is nothing to stop or slow movement of piston and rod assembly 32 from its rearward to its forward position in response to the compressed gas-charge. In the case of the device comprising remote portion 202 and hand-held portion 200, user activation of the trigger may be effected on either remote portion 202 or hand-held portion 200 or both. As depicted in FIGS. 8 and 9, lever 220 is a conventional finger trigger within hand-held portion 200 and is connected to remote portion 202 via trigger cable 206. A non-limiting example of trigger cable 206 is a steel cable, optionally slidably contained within a plastic housing. It will be apparent to the skilled worked that various types of cables are suitable for use as trigger cable 206.

In contrast to the injection device of the present invention, previous injectors required that the trigger be depressed during the entire course of the injection. In such injectors, if the user stops depressing the trigger, the injection process ceases. Therefore, these prior devices can result in incomplete administration of the desired dose of the medicament due to user error in using the trigger.

In accordance with one embodiment of the present invention, the injection device includes trigger guard 23, which is designed to minimize or eliminate the possibility of unintentional triggering of the actuated device.

In accordance with another embodiment of the present invention, the injection device includes a securing latch to maintain handle 3 in the first, closed position until un-latched for use. The securing latch may comprise a moveable downwardly facing hook on the underside of handle 3 that interacts with an upwardly facing hook on the outer surface of housing 1. By moving the downwardly facing hook, the securing latch is released and handle 3 can be moved to its second, open position. Alternatively, the securing latch may comprise a slot in handle 3 for receiving a depressible knob on the outer surface of housing 1. By depressing the knob, the securing latch is released and handle 3 can be moved to its second, open position.

FIGS. 11-21 and 22-25 depict needle-free injection devices according to alternative embodiments of the present invention, which include a manual or motorized means for moving the piston and rod assembly from its forward position to its rearward position. In each case, the device includes a means for transferring and/or amplifying the force applied to the injection device for charging the actuating device. In accordance with a specific embodiment of the present invention, the means for transferring and/or amplifying the applied force comprises a gear assembly; examples of which are depicted in FIGS. 11-21 and 22-25. Such a gear assembly provides a mechanical advantage to facilitate charging of the actuation device. The actuation device of the needle-free injectors depicted in FIGS. 11-21 and 22-25 comprises an actuating member operatively associated with the rod of said piston and rod assembly. The manual or motorized means for moving the piston and rod assembly transfers a force to a gear assembly, which, in turn, transfers, and optionally amplifies, the force to the actuating member to move the piston and rod assembly from the forward position to the rearward position.

As discussed above, actuating device 40 of the needle free injection device of the present invention further comprises means for moving piston and rod assembly 32, against the gas charge in gas tight chamber 4, from its forward to its rearward position. The means for moving piston and rod assembly 32 may be motorized or manual means.

Referring to FIGS. 11-21, actuating device 40 is disposed within guide tube 348, which is connected to dosing reservoir 16 via connector 390. Connector 390 is a generally open-ended cylinder that has a first end, for removable attachment to guide tube 348, and a second end, for removable attachment to dosing reservoir 16. Optionally, connector 390 is removably attached to guide tube 348 via a threaded connection. Similarly, connector 390 is optionally removably attached to dosing reservoir 16 via a threaded connection.

In an alternative embodiment, connector 390 is removably attached to dosing reservoir 16 via a quarter-turn release mechanism. In such a quarter-turn release mechanism, connector 390 further includes two pins (not shown) projecting from the inner surface of connector 390. In this example, dosing reservoir 16 includes a generally L-shaped groove in its outer surface. The protruding pins and generally L-shaped groove are configured to slidingly mate with each other when dosing reservoir 16 is inserted into connector 390, and rotated, such that the pins follow the generally L-shaped groove. In the quarter-turn release mechanism, barrel wave spring 400 is disposed between connector 390 and dosing reservoir 16 so as to urge the connector 390 and dosing reservoir 16 apart, and prevent free rotation of connector 390 and dosing reservoir 16.

Plunger 15 is disposed within dosing reservoir 16 and is removably attached to gap-coupling 13. In one example, plunger 15 is attached to gap-coupling 13 by a threaded screw. In another example, plunger 15 is attached to gap-coupling 13 by a quarter-turn mechanism. Gap-coupling 13 is removably attached to piston 30 of piston and rod assembly 32. Idler pulley 316 is slidingly mounted in guide tube 348 and is attached to gap-coupling 13.

Charging

As described above, movement of piston and rod assembly 32 from its forward position to its rearward position charges the injection device. In use, the injection device depicted in FIGS. 11 to 21, is charged by moving idler pulley 316 from a forward position to a rearward position, which in turn moves piston and rod assembly 32 from its forward to its rearward position. Accordingly, in the device depicted in FIGS. 11-21, idler pulley 316 is serving as an actuating member, as described above.

As noted above, a gear assembly provides a mechanical advantage to facilitate charging of the actuator. In accordance with one embodiment of the present invention, an actuating force is applied by the user to manual means for moving the rod and piston assembly 32. In the specific embodiment depicted in FIGS. 11 to 21, the manual means comprises charging handle 300, which is attached to bracket 364, which is, in turn, pivotally attached to main shaft 302 by a ratchet mechanism 311. Charging handle 300 is pivotable from a first closed position (as depicted in FIGS. 11, 16, 17, 18 and 19) to a second open position (not shown). Main shaft 302 is mounted through gear end 308, and includes first end 301 and second end 303. When charging handle 300 is pivoted, charging handle 300 and bracket 364 rotate main shaft 302.

Ratchet mechanism 311 and pawl 313 that engages ratchet mechanism 311 are configured to permit main shaft 302 to rotate when charging handle 300 is moved from the first closed position to the second open position, and prevent main shaft 302 from rotating when charging handle 300 is moved from the second open position to the first closed position. Other suitable ratchet mechanisms will be well known to the skilled worker and can be incorporated into a needle-free injection device of the present invention.

Main gear 310 is attached to first end 301 of main shaft 302; main pulley 312 is attached to second end 303 of main shaft 302. Both main gear 310 and main pulley 312 rotate with main shaft 302. Cable 314 passes around idler pulley 316, and includes first end 315 attached to main pulley 312 and a second end (not shown) attached to main gear end 308. Cable 314 is constructed of steel and/or other suitable material(s).

Gears is operable to move idler pulley 316 from a forward position to a rearward position, and thereby move piston and rod assembly 32 from its forward position to its rearward position.

Main pulley 312 is rotatable from a first unwound position to an second wound position. As main pulley 312 is rotated from the first unwound position to the second wound position, cable 314 winds around main pulley 312 and pulls idler pulley 316, thereby moving piston and rod assembly 32 from its forward position to its rearward position, against the gas charge in gas tight chamber 4.

In this example, the trigger is a trigger mechanism that releasably retains piston and rod assembly 32 in its rearward position.

Trigger pivot arm 328 is pivotable about secondary shaft 332 from a locked position to an unlocked position. Triggering gear 326 is mounted on trigger pivot arm 328; when trigger pivot arm 328 is in the locked position, triggering gear 326 is in gearing relation with main gear 310. In the locked position, triggering gear 326 rotates as main gear 310 rotates.

Drive gear 330 is mounted on secondary shaft 332, and is also in gearing relation with trigger gear 326; as trigger gear 326 rotates, drive gear 330 rotates.

A uni-directional clutch (not shown, but generally indicated at position 336) allows secondary shaft 332 to rotate when charge handle 300 is move from the first closed position to the second open position. Thus, uni-directional clutch 336 holds the charge of actuating device 40 by preventing main shaft 302 and secondary shaft 332 from rotating, when charging handle 300 has moved from the first closed position to the second open position.

Repeated movement of charging handle 300 from the first closed position to the second open position, and back, results in the continued winding of main pulley 312, and movement of piston and rod assembly 32 to the rearward position, against the gas charge in gas tight chamber 4.

Charging of actuating device 40 continues until the desired charge is achieved. In one example, a dosage ring (not shown) is used to set the desired charge. In this example, the dosage ring is positioned on guide tube 348 and can be locked into place. The dosage ring is user adjustable to set the extent to which piston and rod assembly 32 can be drawn back; therefore, the dosage ring is user adjustable to set the amount of medicament that is ultimately drawn in to the injector, for subsequent injection. The dosage ring may be set to include a wide range of charges, and thus injection volumes. In one example, the dosage ring is adjustable over a range of volumes between about 0.01 cc to about 5 cc.

When trigger pivot arm 328 is moved to the unlocked position, triggering gear 326 pivots away from main gear 310, enabling main gear 310 and main shaft 302 to rotate so as to permit main pulley 312 to move from the second wound position to the first unwound position. Movement of main pulley 312 from the second wound position to the first unwound position permits piston and rod assembly 32 to move from its rearward position to its forward position, due to the pressure generated by the compressed gas-charge.

Trigger pivot arm 328 is operably connected to barrel trigger 356 or finger trigger 354 though a series of trigger levers and a trigger rod. First trigger lever 338 is pivotally attached to trigger pivot arm 328 and second trigger lever 340. Second trigger lever 340 is pivotally attached to pivot mount 380. Second trigger lever 340 includes slot 366. Third trigger lever 342 is pivotally mounted to main gear end 308, at pivot mount 368. First end 343 of third trigger lever 342 is slidingly attached to second trigger lever 340 at slot 366; second end 345 of third trigger lever 342 is attached to fourth trigger lever 344. Fourth trigger lever 344 is pivotally mounted to third trigger lever 342 at pivot mount 370, and is attached to first end 307 of main triggering rod 306.

Main trigger rod 306 is slidingly mounted through trigger rod guides 346, which are attached to guide tube 348. Main trigger rod 306 is movable between a forward position to a rearward position. In the forward position, trigger pivot arm 328 is in the locked position; in the rearward position, trigger pivot arm 328 is moved to the unlocked position. Finger trigger linkage 350 has a first end that is attached to main trigger rod 306 and a second end that is attached to finger trigger 354. Barrel trigger 356 is slidingly mounted on reservoir 16. Barrel spring 352 urges barrel trigger 356 away from second end 309 of main trigger rod 306. Actuation of the needle free injector can be accomplished using barrel trigger 356 or finger trigger 354.

Using barrel trigger 356, nozzle 17 is pushed onto the body to be injected with enough force to move barrel trigger 356 against barrel spring 352 so as contact and move main trigger rod 306 from its forward position to its rearward position.

Using finger trigger 354, moving finger trigger 354 from a forward position to a rearward position causes finger trigger linkage 350 to move main trigger rod 306 from its forward position to its rearward position.

Movement of main trigger rod 306 from its forward position to its rearward position causes in fourth trigger lever 344, third trigger lever 342, second trigger lever 350 and first trigger lever 338 to act so as to move trigger pivot arm 328 from the locked position to the unlocked position. As discussed above, movement of trigger pivot arm 328 to the unlocked position allows main gear 310 and main shaft 302 to rotate so as to permit main pulley 312 to move from the second wound position to the first unwound position. Movement of main pulley 312 from the second wound position to the first unwound position permits piston and rod assembly 32 to move from its rearward position to its forward position, due to the pressure generated by the compressed gas-charge.

Following injection, a spring (not shown) urges finger trigger 350 from its rearward position to its forward position.

Movement of finger trigger 350 to its forward position results in movement of main trigger rod 306 from its rearward to its forward position, and movement of trigger pivot arm 328 from its unlocked position to its locked position. The user is now able to repeat the charging procedure.

Alternatively, barrel trigger 356 is urged from its rearward position to its forward position by barrel trigger spring 352. A mechanical spring between trigger pivot arm 328 and first trigger lever 338 (not shown) pulls these parts together, thereby moving trigger pivot arm 328 from the released position to the locked position.

A trigger safety is optionally included. In this embodiment, trigger safety 304 is movable from a locked position to an unlocked position. When charging handle 300 is moved from the first closed position to the second open position, main shaft 302 rotates and causes trigger safety 304 to move from an unlocked position to a locked position. In the locked position, trigger safety 304 prevents main triggering rod 306 from moving to its rearward position. Trigger safety 304 is pivotally mounted on main gear end 308, and has two springs (not shown) that urge trigger safety 304 to the locked position. Trigger safety 304 moves from the locked position to the unlocked position when charging handle 300 is moved to its first closed position. Ratchet mechanism 311 and pawl 313 act on trigger safety 304, so as to enable main trigger rod 306 to move to its rearward position.

The needle-free injector depicted in FIGS. 11-21 can also be actuated using a motorized means for charging. In the case of motorized charging, charging handle 300 can remain in place or be removed. If charging handle 300 remains in place, a ratchet mechanism (not shown) is included and permits for normal operation of injector by gear motor 360. Additionally, if charging handle 300 is present, trigger safety 304 is deactivated using a safety deactivating cap (not shown).

In accordance with one embodiment of the present invention, gear motor 360 is a DC gear motor that is powered by a battery, such as a re-chargeable battery. Optionally, the battery is located in battery mount 358. A user activates gear motor 360 using a rocker switch (not shown), which allows electricity from the battery to flow to gear motor 360. Gear motor 360 rotates pinion gear 362, which rotates crown gear 334. Secondary shaft 332 rotates drive gear 300 (as described above), which rotates triggering gear 326. Main gear 310 rotates main pulley 312, which winds cable 314, thereby moving piston and rod assembly 32 from the forward to the rearward position.

In this embodiment, the dosage ring (not shown) includes an electric limit switch (not shown), which once reached by the gap coupling 13 and piston and rod assembly 32, interrupts the flow of electricity to gear motor 360, thereby stopping charging. The load is held by same uni-directional clutch 336 on secondary shaft 332, as described for manual charging.

Triggering is accomplished in the same manner as described in manual charging, using either barrel trigger 356 or finger trigger 354.

Once piston and rod assembly 32 has returned to the forward position, a second electrical switch (not shown) is activated, which allows gear motor 360 to start and recharge the unit again.

A third electrical switch (not shown) is mounted on finger trigger 354, which acts as a safety switch. Finger trigger 354 must be in its forward position (or released from any pushing or squeezing) for motor 360 to restart. This is to insure that triggering gear 326 and main gear 310 are engaged before the gear motor 360 starts.

FIGS. 22-25 depict a needle-free injector according to another embodiment of the present invention. The injector depicted in FIGS. 22-25 also includes a gear assembly to transfer and/or amplify an actuation force applied to the injector for moving the piston and rod assembly against the gas charge. The gear assembly is operatively associated with either a manual means or motorized means for moving the piston and rod assembly in order to provide a mechanical advantage to facilitate charging of the actuator. The injector depicted in FIGS. 22-25 further includes an actuating member operatively associated with the rod of said piston and rod assembly. Whereby, said manual means or said motorized means transfers a force to said gear assembly which transfers the force to said actuating member to move said piston and rod assembly from the forward position to the rearward position.

Referring to FIGS. 22-25, housing 1 is removably connected to reservoir 16. Actuating device 40 is disposed within guide tube 348 in housing 1. Union connector 504 is removably attached to guide tube 248 and acts as a gap-coupling. Piston and rod assembly 32 of actuating device 40 is removably attached to guide tube 348. Piston 15 is slidingly disposed within reservoir 16 and is slidingly attached to union coupler 502. Gear rack 504 is attached the outer surface of guide tube 348, and is slidingly disposed within slot 506 of housing 1.

As described above, movement of piston and rod assembly 32 from its forward position to its rearward position charges actuation device 40. In the device depicted in FIGS. 22 to 24, charging of the injector is achieved by moving gear rack 504 from a forward position to a rearward position, which in turn moves piston and rod assembly 32 from its forward to its rearward position. Accordingly, gear rack 504 is serving as an actuating member.

In accordance with one embodiment of the present invention, gear motor 360 rotates pinion gear 362, which rotates crown gear 334. Crown gear 334 is attached to a first end of shaft 506 and gear 508 is attached to a second end of shaft 506; gear 508 rotates as crown gear 334 rotates. Shaft 506 is mounted in gear mount 509, which is attached to housing 1.

Gear 508 rotates idler gear 510, which rotates compound gear 512. Compound gear 512 includes outer gear 514 and inner gear 516. Idler gear 510 rotationally engages outer gear 514. Inner gear 516 rotationally engages charging gear 520. Rotation of compound gear 512 rotates charging gear 520.

Charging gear 520 includes first gear 518 and recessed second gear (not shown, but generally indicated by the line denoted by numeral 522). Charging gear 520 is rotationally attached to clutch mount 540; clutch mount 540 is pivotally attached to housing 1 at attachment mount 542. Charging gear 520 is movable between an charging position and a release position. In the charging position, first gear 518 of charging gear 520 engages gear rack 504 and is operable to move gear rack 540 from its forward to its rearward position, thereby moving piston and rod assembly 32 against from the forward to rearward position, and charge actuating device 40. Recessed second gear 522 rotationally engages locking gear 524, which is attached to uni-direction clutch 336.

Uni-directional clutch 336 and locking gear 524 enable charging gear 520 to rotate when moving gear rack 504 from its forward position to its rearward position, and does not allow charging gear 520 to rotate so as to move gear rack 504 from its rearward to its forward position. Thus, uni-directional clutch 336 holds the charge of actuating device 40.

Charging of actuating device 40 continues until the desired charge is achieved. In one example, dosage ring 526 is used to set the desired charge. In this example, dosage ring 526 is positioned on housing 1 at a user determined position, and can be locked into place. Dosage ring 526 includes guide 528 for receiving gear rack 504. Guide 528 includes gearing teeth (not shown) on the inner surface that matingly engage with gear rack 504. When dosage ring 526 is locked on housing 1 and gear rack 504, the extent to which gear rack 504 and piston and rod assembly 32 can be drawn back is user determined; therefore, the dosage ring is user adjustable to set the amount of medicament that is ultimately drawn in to the injector, for subsequent injection. The dosage ring may be set to include a wide range of charges, and thus injection volumes. In one example, the dosage ring is adjustable over a range of volumes between about 0.01 cc to about 5 cc.

When charging gear 520 is moved from its charging position to its release position, charging gear 520 disengages gear rack 504, permitting gear rack 504 to move from its rearward position to its forward position.

In this example, the trigger is a trigger mechanism that releasably retains piston and rod assembly 32 in its rearward position.

Figure 22:
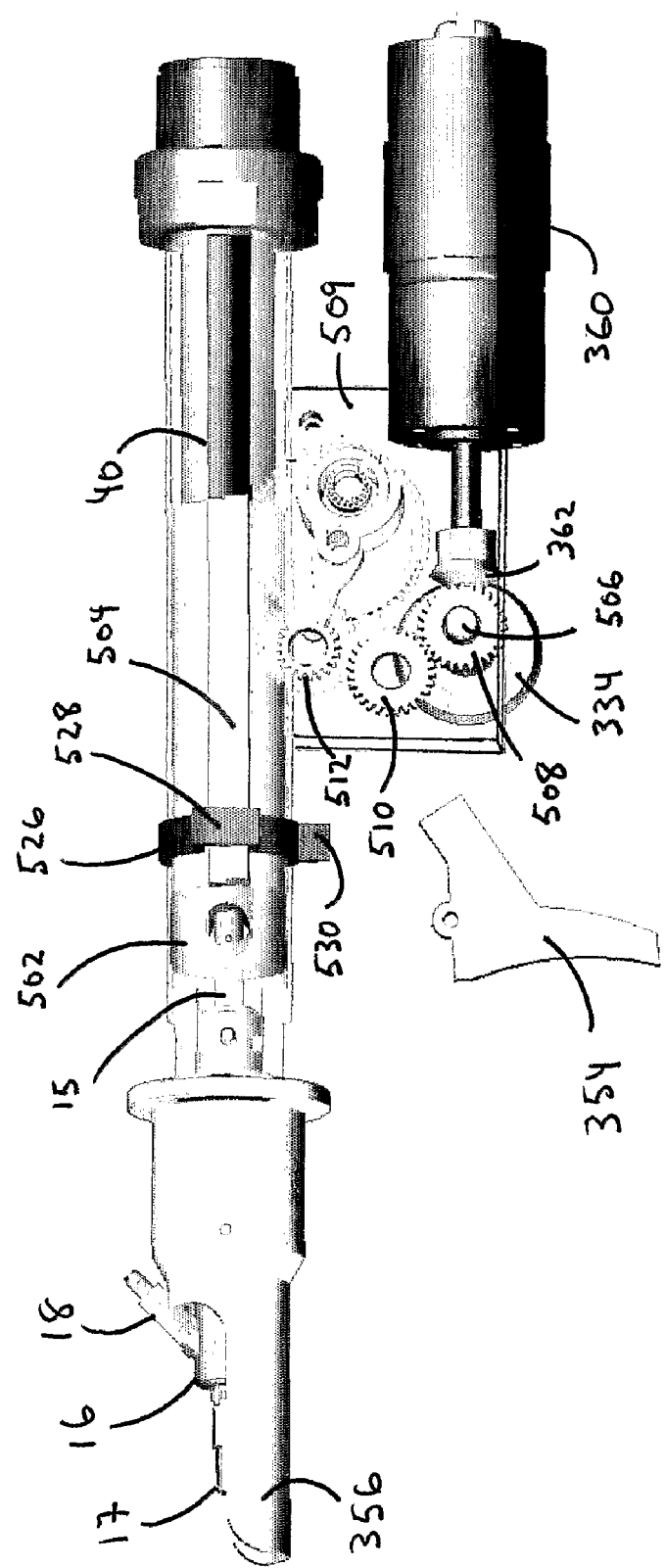
FIG. 22 is a partially transparent side view of a needle-free injection device according to an alternative embodiment of the present invention.
Figure 23:
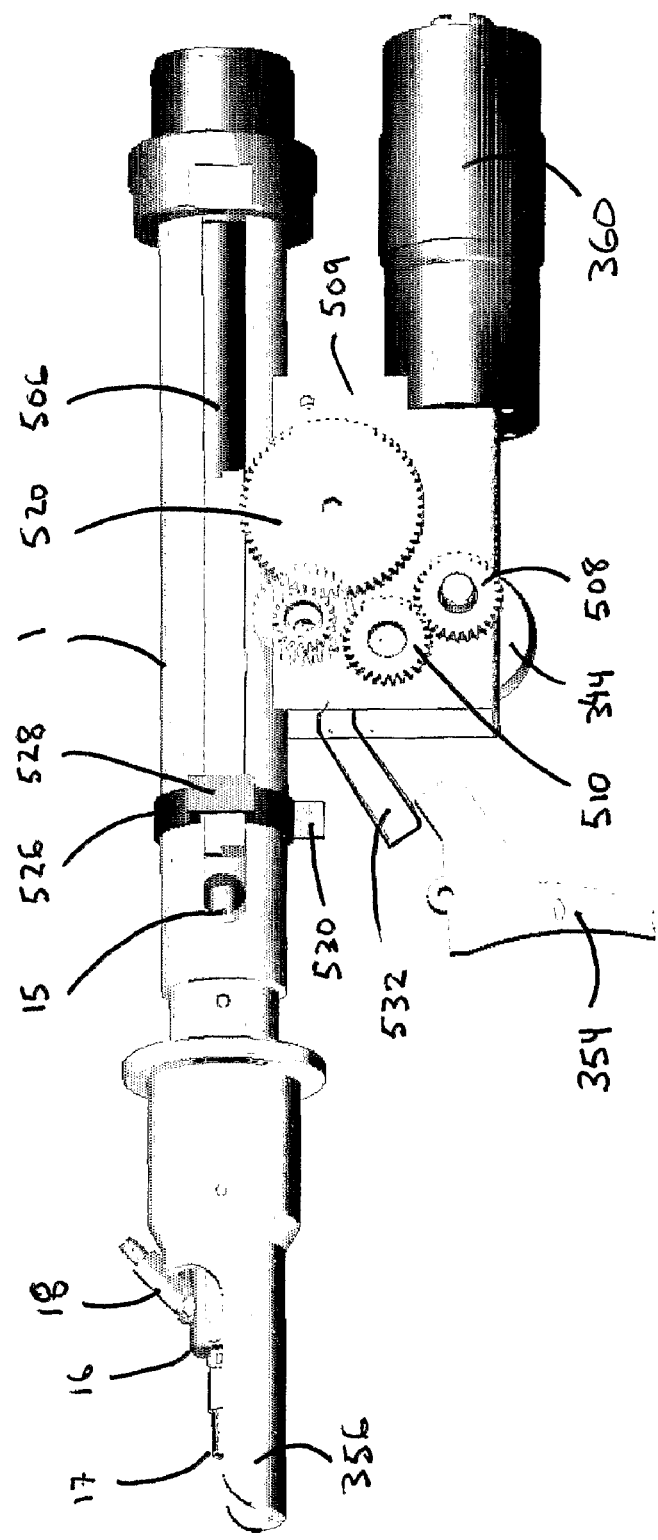
FIG. 23 is a side view of the needle-free injection device depicted in FIG. 22.
Figure 24:
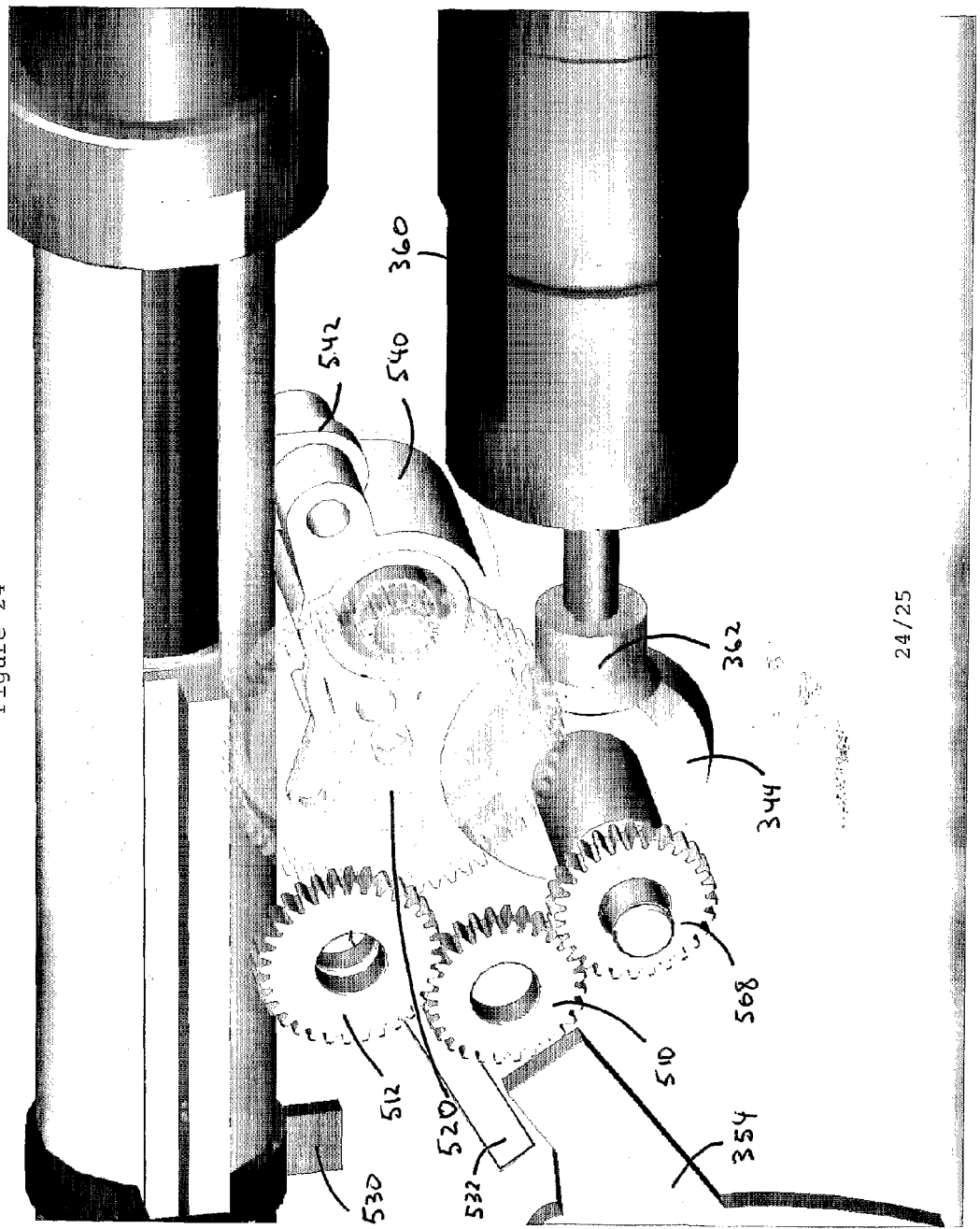
FIG. 24 is a magnified side view of the needle-free injection device depicted in FIG. 22.
Figure 25:
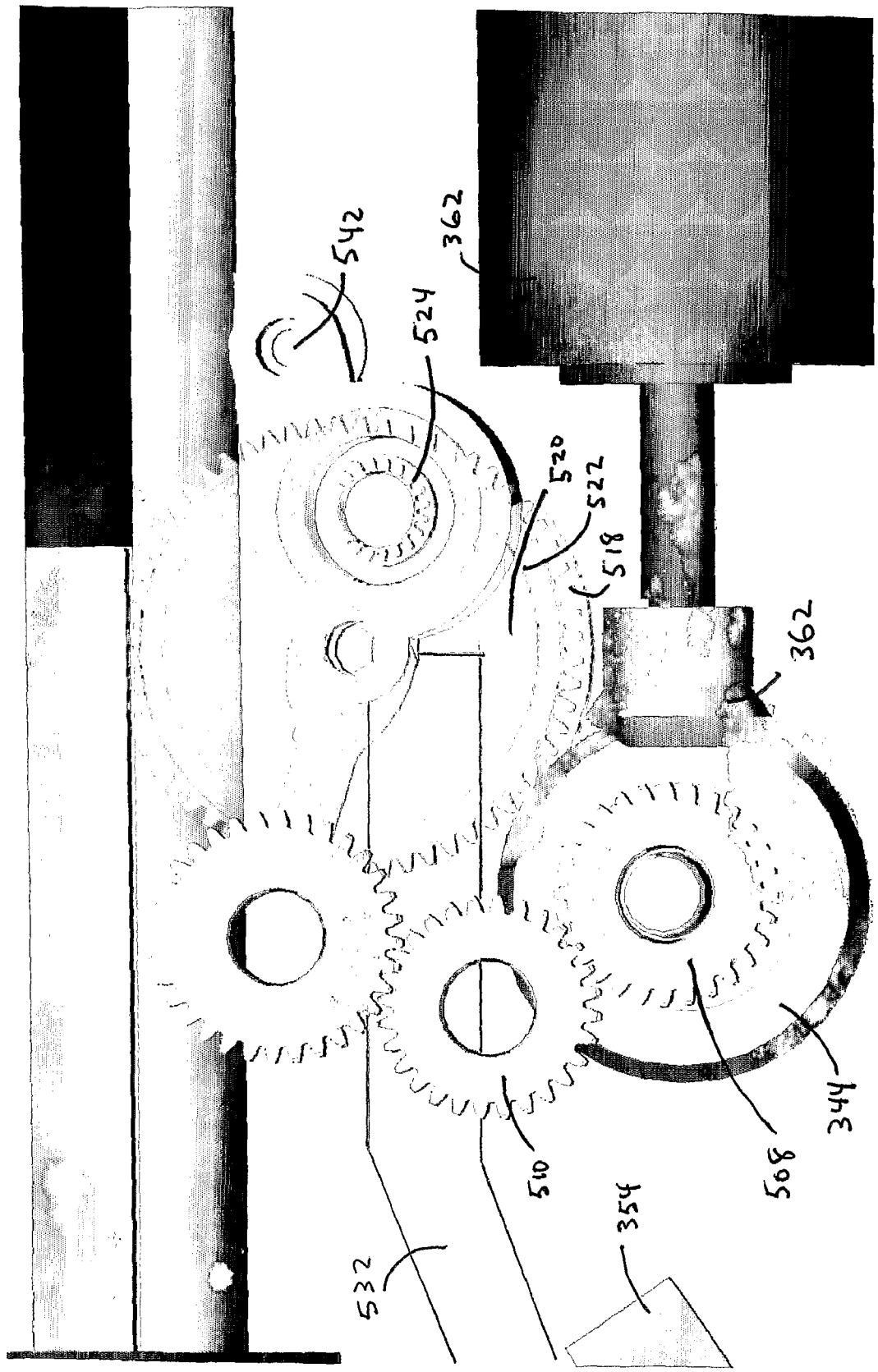
FIG. 25 is a magnified side view of the needle-free injection device depicted in of FIG. 22.

Charging gear 520 is operably connected to barrel trigger 356 or finger trigger 354 by trigger release 532. Trigger release 532 is attached to clutch mount 540 and is operable to move charging gear 520 between its charging position and its release position. In the example of FIG. 22-24, dosage ring 526 includes trigger catch 530, which is configured to releasably engages trigger release 532. When gear rack 504 has been moved to its rearward position, trigger catch 530 engages trigger release 532. Following attachment of trigger catch 530 to trigger release 532, charging gear 520 is moved from its charging position to its release position. Accordingly, the charge within actuation device 40 is held in place by the attachment of trigger catch 530 to trigger release 532.

Actuation of the needle free injector is accomplished using barrel trigger 356 or finger trigger 354. In each instance, actuation is achieved by moving trigger release 532 so as disengage trigger catch 530 from trigger release 532, thereby permitting gear rack 504 to move from its rearward position to its forward position. Using finger trigger 354, depressing finger trigger 354 causes disengagement of trigger catch 530 from trigger release 532. Using barrel trigger 356, nozzle 17 is pushed onto the body to be injected with enough force to move barrel trigger 356 against a barrel spring (not shown) so as to cause disengagement of trigger catch 530 from trigger release 532.

In an alternative embodiment, the needle free injector depicted in FIGS. 22-24 is adapted for suited to manual charging. In the case of manual charging, gear motor 360 is not used. Instead, a charging handle and ratchet mechanism (not shown) directly or indirectly rotate gear 506. In the case of indirect rotation of gear 506, a chain gear is optionally used to connect the charging handle and ratchet mechanism to gear 506. Charging and actuation is carried out as described above.

It will be clear to the skilled worker that various arrangement of gears and gearing can be used in a gear assembly to increase the mechanical advantage for charging actuating device 40. For example, a "gear train" consisting of several gears acting on each other can drive a rack and pinion, which acts directly or indirectly on piston and rod assembly 32 to move piston and rod assembly to its rearward position. A planetary drive gear box can be used to act on the directly or indirectly on piston and rod assembly 32, in a similar fashion. Similarly, a planetary gear box and ratchet system may be used. The use of a worm gear drive is another alternative. Any combination of or set up of any suitable individual "gear option" can increase the mechanical advantage several times, thereby reducing the force charge actuating device 40. The addition and use of such "gear trains" makes it easier for users to charge actuating device 40.

As would be readily appreciated by a worker skilled in the art, the positioning of the nozzle against the subject will depend on a number of factors, including, but not limited to, the species and body region to be injected, the age of the subject to be injected, and the pressure of the gas charge. For example, certain animal species will have skin that is more D difficult to pierce than others. This is due, in part, to species differences in skin thickness. Additionally, members of a particular species will have regions of the body that are more or less difficult to inject. The age of the animal and or human may also have an effect on the ease of injection, since skin thickness and coarseness can vary with age. For example, in some species, a younger individual (e.g., neonate or infant) will have skin that is more readily injectable than an adult individual. As well, in a variety of animals, for example, regions behind the ears or in creases of limbs will typically be easier to inject. Those body regions that are more readily injected will require a lower pressure gas charge compared to a body region that is more difficult to inject. The skilled worker will appreciate and take into consideration the various species, body region and/or age differences, when selecting the pressure of the gas-charge.

The injection device of the present invention optionally includes a supply reservoir for supplying liquid to dosing reservoir 16. In a specific, non-limiting example, as depicted in FIGS. 2 and 9, supply reservoir is syringe 21 containing a medicament. In FIG. 8 the supply reservoir is bottle 208 containing a medicament. Syringe 21 and bottle 208 are connected to dosing reservoir 16 by a length of tubing 19 and a one-way valve 18. One-way valve 18 allows unidirectional movement of medicament from syringe 24 to dosing reservoir 16. In these embodiments movement of plunger 15 from the forward position to the rearward position in dosing reservoir 16 causes a single dose of medicament to be drawn from syringe 21 into dosing reservoir 16.

In accordance with another aspect of the present invention there is provided a method of using the needle-free injection device for injection of a liquid through the skin of a subject, that may be an animal or human. The method comprises the steps of (i) providing a needle-free injection device of the present invention having at least one dose of the liquid to be administered; (ii) actuating the device by moving piston and rod assembly 32 to the rearward position; placing nozzle 17 against the skin of the subject to be injected; and (iii) triggering the actuation device to expel a dose of the liquid through the outlet orifice and nozzle 17 and through the skin of the subject.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. In a needle-free injection device for delivering a medicament under pressure from a dosing reservoir through an outlet orifice for administration to an animal or human, of the type comprising a plunger slidably received in said dosing reservoir and movable in a forward direction for expelling said medicament through said orifice, the improvement comprising an actuating device, said actuating device comprising:
   (a) a gas tight chamber;
   (b) a piston and rod assembly slidably received in said chamber and movable between a forward position and a rearward position;
   (c) a gas charge in said chamber for urging said piston and rod assembly to said forward position;
   (d) means for moving said piston and rod assembly against said gas charge into said rearward position; and
   (e) a trigger for releasably retaining said piston and assembly in said rearward position wherein said trigger comprises a triggering lever having a first end and a second end and being pivotable about a pivot member and connected at said first end to a push rod, whereby when a downward force is exerted on said second end of said triggering lever it pivots about said pivot member and said first end is raised causing said push rod to disengage said actuating member such that said piston and rod assembly moves from said rearward position to said forward position, whereby activating said trigger causes said piston and rod assembly to be released for movement by said gas charge to said forward position so as to impact said plunger directly or indirectly with a force sufficient to cause said plunger to move in said forward direction to expel said medicament through said outlet and whereby said gas tight chamber is adapted to minimize or prevent the escape of said gas charge so as to maintain said gas charge in a pressurized state.

2. The needle-free injection device according to claim 1, wherein the circumference of the piston of said piston and rod assembly defines an outer edge that is in contact with the interior surface of said gas tight chamber such that the piston defines an extension portion and a compression portion of said gas tight chamber.

3. The needle-free injection device according to claim 2, wherein said piston of said piston and rod assembly comprises a passage for fluid communication between said extension portion and said compression portion of the gas tight chamber.

4. The needle-free injection device according to claim 1, wherein said gas charge is a compressed inert gas or a mixture of compressed inert gas.

5. The needle-free injection device of claim 4, wherein the compressed inert gas is nitrogen.

6. The needle-free injection device according to claim 1 further comprising a lubrication medium for lubricating said piston and rod assembly.

7. The needle-free device according to claim 6, wherein lubrication medium is a light weight oil.

8. The needle-free injection device according to claim 1 further comprising a gap-coupling connecting the rod of said piston and rod to the plunger, wherein said gap-coupling is configured to maintain a gap-distance between said rod and said plunger when said piston and rod assembly is in said rearward position.

9. The needle-free injection device of claim 8 wherein the gap-coupling comprises:
   (a) a first end for removable attachment of the gap-coupling to said rod; and
   (b) a second end for sliding engagement with the plunger.

10. The needle-free device according to claim 1 further comprising means for transferring force generated by movement of said piston and rod assembly to said plunger, whereby activating said trigger causes said piston and rod assembly to be released for movement by said gas charge to said forward position thereby imparting a force to said means for transferring force which in turn imparts the force to said plunger sufficient to cause said plunger to move in said forward direction to expel said medicament through said outlet.

11. The needle-free injection device according to claim 1, wherein said means for moving said piston and rod assembly is a manual means.

12. The needle-free injection device according to claim 11, wherein said manual means comprises:
    (a) a handle pivotally connected to said needle-free injection device and pivotable from a first closed position to a second open position;
    (b) a push rod pivotally attached to said handle; and
    (c) an actuating member operatively associated with the rod of said piston and rod assembly,
whereby when said handle is moved from said first closed position to said second open position said push rod engages said actuating member and when said handle is returned to said closed position a pushing force is transferred to said push rod, which in turn transfers the pushing force to said actuating member to move said piston and rod assembly from said forward position to said rearward position.

13. The needle-free injection device of claim 1 wherein said means for moving said piston and rod assembly is a motorized means.

14. The needle-free injection device according to claim 13 further comprising:
    (a) a gear assembly operatively associated with said motorized means; and
    (b) an actuating member operatively associated with the rod of said piston and rod assembly,
whereby said motorized means transfers a force to said gear assembly which transfers the force to said actuating member to move said piston and rod assembly from said forward position to said rearward position.

15. The needle-free injection device of claim 13 wherein said motorized means is a DC power supply.

16. The needle-free injection device of claim 13 wherein said motorized means is an AC power supply.

17. The needle-free injection device according to claim 12, wherein the push rod is adjustable in length.

18. The needle-free injection device according to claim 11, wherein said manual means comprises:
    (a) a handle pivotally connected to said needle-free injection device and pivotable from a first closed position to a second open position;
    (b) a gear assembly operatively associated with said handle; and
    (c) an actuating member operatively associated with the rod of said piston and rod assembly,
whereby when said handle is moved from said first closed position to said second open position said gear assembly transfers a force to said actuating member to move said piston and rod assembly from said forward position to said rearward position.

19. The needle-free injection device according to claim 18, wherein said trigger comprises a trigger mechanism, whereby user activation of said trigger mechanism causes said gear assembly to disengage said actuating member such that said piston and rod assembly moves from said rearward position to said forward position.

20. A method of injecting a medicament into an animal or a human, comprising:
    (a) providing an actuated needle-free injection-device according to claim 1 having a medicament within said dosing chamber;
    (b) placing the outlet orifice against said animal at a site for administration; and
    (c) triggering said injection-device such that said medicament is expelled through said outlet orifice.

21. A kit for the use of the needle-free injection device according to claim 1, comprising:
    (a) the needle-free injection device; and
    (b) instructions for the use thereof.

* * * * *

UNITED STATES PATENT AND TRADEMARK OFFICE
CERTIFICATE OF CORRECTION

PATENT NO. : 8,221,347 B2
APPLICATION NO. : 11/792141
DATED : July 17, 2012
INVENTOR(S) : Warren L. Toles et al.

It is certified that error appears in the above-identified patent and that said Letters Patent is hereby corrected as shown below:

Column 18, line 21, "said actuating member" should read -- an actuating member --;

Column 18, line 33, "contact with the" should read -- contact with an --;

Column 19, line 15, "(c) an actuating member" should read -- (c) said actuating member --;

Column 19, line 31, "(b) an actuating member" should read -- (b) said actuating member --; and Column 20, line 12, "(c) an actuating member" should read -- (c) said actuating member --.

Signed and Sealed this
Second Day of April, 2013

Teresa Stanek Rea
*Acting Director of the United States Patent and Trademark Office*